US009691258B2

United States Patent
Sloo et al.

(10) Patent No.: US 9,691,258 B2
(45) Date of Patent: *Jun. 27, 2017

(54) SMART HAZARD DETECTOR PROVIDING FOLLOW UP COMMUNICATIONS TO DETECTION EVENTS

(71) Applicant: Google Inc., Mountain View, CA (US)

(72) Inventors: David Sloo, Menlo Park, CA (US); Nicholas Unger Webb, Menlo Park, CA (US); Matthew Lee Rogers, Los Gatos, CA (US); Anthony Michael Fadell, Portola Valley, CA (US); Jeffery Theodore Lee, Mountain View, CA (US); Sophie Le Guen, Burlingame, CA (US); Andrew W. Goldenson, Palo Alto, CA (US)

(73) Assignee: Google Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/875,503

(22) Filed: Oct. 5, 2015

(65) Prior Publication Data

US 2016/0104366 A1 Apr. 14, 2016

Related U.S. Application Data

(63) Continuation of application No. 14/617,619, filed on Feb. 9, 2015, now Pat. No. 9,189,946, which is a (Continued)

(51) Int. Cl.
G08B 17/10 (2006.01)
G08B 25/00 (2006.01)
(Continued)

(52) U.S. Cl.
CPC ........ *G08B 25/008* (2013.01); *F24F 11/0009* (2013.01); *G01N 27/02* (2013.01);
(Continued)

(58) Field of Classification Search
CPC ...... G08B 17/00; G08B 17/10; G08B 17/125; G08B 21/182; G08B 25/001
(Continued)

(56) References Cited

U.S. PATENT DOCUMENTS 5,376,924 A * 12/1994 Kubo ................... G08B 17/117
340/522
5,686,896 A 11/1997 Bergman
(Continued)

FOREIGN PATENT DOCUMENTS

WO 2015/054278 4/2015

OTHER PUBLICATIONS

International Search Report and Written Opinion mailed Jan. 5, 2015 for International Patent Application PCT/US2014/59526 filed Oct. 7, 2014, all pages.

(Continued)

*Primary Examiner* — Phung Nguyen
(74) *Attorney, Agent, or Firm* — Kilpatrick Townsend & Stockton LLP

(57) ABSTRACT

Ambient amount of a hazardous condition may be monitored. A mode may be set to a state indicative of the hazardous condition being present in the ambient environment. It may then be determined that the amount of the hazard in the ambient environment has dropped below an alarm criterion. A time period may then be tracked during which the amount of the hazardous condition present in the ambient environment of the hazard detector has remained below the alarm criterion. It may be determined that the time period has reached at least a threshold duration, during such time period the amount of the hazardous condition present in the ambient environment of the hazard detector having remained below the alarm criterion. An indication of the (Continued)

hazardous condition easing may be output in response to the time period being at least the threshold duration.

18 Claims, 20 Drawing Sheets

Related U.S. Application Data continuation of application No. 14/508,146, filed on Oct. 7, 2014, now Pat. No. 8,988,232.

(60) Provisional application No. 61/887,969, filed on Oct. 7, 2013, provisional application No. 61/887,963, filed on Oct. 7, 2013.

(51) Int. Cl.
| | | |
|---|---|---|
| *G01N 27/02* | (2006.01) | |
| *G01N 27/12* | (2006.01) | |
| *G01N 33/00* | (2006.01) | |
| *G08B 21/18* | (2006.01) | |
| *G08B 29/18* | (2006.01) | |
| *G08B 5/36* | (2006.01) | |
| *G08B 3/10* | (2006.01) | |
| *G08B 21/14* | (2006.01) | |
| *H04L 12/28* | (2006.01) | |
| *G08B 5/22* | (2006.01) | |
| *G08B 21/12* | (2006.01) | |
| *F24F 11/00* | (2006.01) | |
| *G08B 25/01* | (2006.01) | |
| *G08B 29/02* | (2006.01) | |
| *G08B 29/04* | (2006.01) | |
| *G08B 29/26* | (2006.01) | |
| *G08B 25/08* | (2006.01) | |

(52) U.S. Cl.
CPC ......... *G01N 27/121* (2013.01); *G01N 33/004* (2013.01); *G01N 33/0031* (2013.01); *G08B 3/10* (2013.01); *G08B 5/22* (2013.01); *G08B 5/36* (2013.01); *G08B 17/10* (2013.01); *G08B 21/12* (2013.01); *G08B 21/14* (2013.01); *G08B 21/18* (2013.01); *G08B 25/002* (2013.01); *G08B 25/012* (2013.01); *G08B 29/02* (2013.01); *G08B 29/04* (2013.01); *G08B 29/185* (2013.01); *G08B 29/26* (2013.01); *H04L 12/2803* (2013.01); *H04L 12/2818* (2013.01); *G08B 25/08* (2013.01)

(58) Field of Classification Search
USPC .... 340/501, 511, 527, 539.1, 577, 588, 628, 340/632, 13.24, 286.05, 309.16
See application file for complete search history.

(56) References Cited

U.S. PATENT DOCUMENTS

| | | |
|---|---|---|
| 6,144,310 A | 11/2000 | Morris |
| 6,166,633 A | 12/2000 | Wang |
| 6,624,750 B1 | 9/2003 | Marman et al. |
| 7,265,678 B2 | 9/2007 | Chapman et al. |
| 8,172,154 B1 | 5/2012 | Figley et al. |
| 8,988,232 B1 | 3/2015 | Sloo et al. |
| 9,189,946 B2 | 11/2015 | Sloo et al. |
| 2002/0044061 A1* | 4/2002 | Johnston .............. G01N 33/004 340/628 |
| 2004/0135695 A1* | 7/2004 | Barton ................. G08B 25/002 340/628 |
| 2004/0140892 A1 | 7/2004 | Hanood |
| 2006/0092012 A1 | 5/2006 | Kaiser et al. |
| 2007/0008158 A1* | 1/2007 | Barrieau ................ G08B 17/00 340/577 |
| 2008/0117067 A1 | 5/2008 | Abel et al. |
| 2010/0271219 A1* | 10/2010 | Lang ..................... G08B 17/10 340/628 |
| 2011/0057806 A1 | 3/2011 | Gonzales |
| 2012/0229285 A1 | 9/2012 | Rauworth et al. |
| 2014/0085093 A1 | 3/2014 | Mittleman et al. |

OTHER PUBLICATIONS

International Preliminary Report on Patentability mailed Apr. 21, 2016, for International Patent Application No. PCT/US2014/059526, 9 pages.

Notice of Publication for European Patent Application No. 14852672.6 mailed Jul. 20, 2016.

* cited by examiner

| Light State | Definition |
|---|---|
| 1201 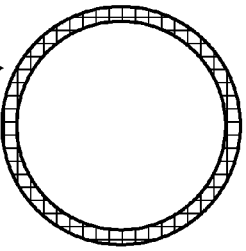<br>(blue) | A blue glow is emitted when awake and ready to be configured.<br><br>Before and after a manual test, a blue glow is emitted. |
| 1202 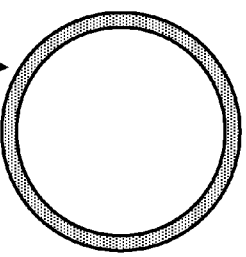<br>(green) | A green pulse is emitted during and after setup to confirm communication with the Internet and to signal that setup is complete.<br><br>A green pulse is emitted at night when the lights are turned off to signal that the batteries and sensors are functioning properly. |
| 1203 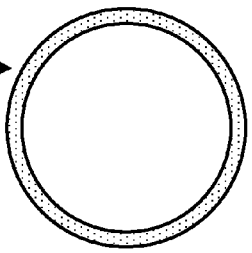<br>(white) | White light is emitted when a path-light feature is triggered, such as based on a detected ambient brightness level below a threshold and user motion being detected. |

FIG. 12

| Light State | Definition |
|---|---|
| 1204 → (yellow) | A low level of smoke or carbon monoxide (CO) has been detected. A "heads-up" (pre-alert) message may be output that indicates the type of danger and the location.<br><br>If a heads-up (pre-alert) message is silenced due to a button press or wave, a yellow glow is output. The device continues to monitor for hazards.<br><br>If a low battery level is detected or a sensor is having a problem or is expired, a pulsed yellow light will be output when the ambient brightness level drops below a threshold level.<br><br>If a manual test is failed, a yellow glow is emitted along with an indication of the problem. |
| 1205 → (red) | A dangerous level of smoke or carbon monoxide has been detected. A loud alarm and voice is output identifying the location and type of problem. The alarm sound and the voice message may be interleaved such that the two outputs alternate being output.<br><br>If the device is silenced by a gesture or button press, the device will remain quiet while outputting a red glow. The structure will continue to be monitored for hazards. |
| 1206 → (green) | A small, separate light may be illuminated when power is being received from a structure's wired electrical system (e.g., 120 V AC). |

FIG. 13

| Light State | Audio Output | Definition |
|---|---|---|
| 1210 → Yellow pulses | Ding/Bell sound interleaved with "Heads-up. There's carbon monoxide in the [room name]. The alarm may sound." | Carbon monoxide levels are rising. |
| 1211 → Yellow pulses | "Alarm Hushed" | The alarm has been silenced temporarily. |
| 1212 → Red pulses | [Alarm sound] interleaved with "Emergency. There's smoke in the [room name]." | The smoke in the room as reached emergency (alert) levels. |

FIG. 15

| Light State | Audio Output | Definition |
|---|---|---|
| 1213 — Red pulses | [Alarm sound] interleaved with "Emergency. There's carbon monoxide in the [room name]. Move to fresh air." | The carbon monoxide in the room as reached emergency (alert) levels. |
| 1214 — Red pulses | "Alarm Hushed" | The alarm has been silenced temporarily. |
| 1215 — Green pulses | "Smoke is clearing in the [room name]." | Conditions are returning to normal. |

FIG. 16

| Light State | Audio Output | Definition |
|---|---|---|
| 1219 → Yellow pulses | "The battery is low in [room name]. Replace the battery soon." | The batteries are low and should be replaced soon. |
| 1220 → Yellow pulses | Two chirps may sound every minute. "The device has expired. Replace it now." | The device has reached the end of its life. |
| 1221 → Yellow pulses | "Disconnected from the Internet" | The device is no longer connected to the Internet. |

FIG. 18

| Type of Alarm | Can be silenced | Cannot be silenced |
|---|---|---|
| Heads-up (pre-alert) for smoke or carbon monoxide | By waving (wave-to-hush gesture) or pressing a button on the device | By regulation (law), a heads-up is permitted to be silenced from the device that triggered the alarm. An alert as to which room is given. |
| Smoke emergency (alert) alarms | By waving (a wave-to-hush gesture) or pressing a button on the device | Dense or dangerous smoke levels will override the alarm being silenced. A continuous alarm will sound. |
| Carbon monoxide emergency (alert) alarms | Can be silenced by waving (wave-to-hush gesture) or pressing a button on the device. If dangerous levels of CO are reached with a predefined period of time (e.g., 6 minutes), the alarm will sound again. | |

FIG. 19

SMART HAZARD DETECTOR PROVIDING FOLLOW UP COMMUNICATIONS TO DETECTION EVENTS

CROSS-REFERENCES TO RELATED APPLICATIONS

This application is a continuation of U.S. patent application Ser. No. 14/617,619, filed Feb. 9, 2015, entitled "Smart-Home Hazard Detector Providing Useful Follow Up Communications To Detection Events," now U.S. Pat. No. 9,189, 946, issued Nov. 17, 2015 which is a continuation of U.S. patent application Ser. No. 14/508,146, filed Oct. 7, 2014, entitled "Smart-Home Hazard Detector Providing Useful Follow Up Communications To Detection Events," now U.S. Pat. No. 8,988,232, issued Mar. 24, 2015, which claims priority to U.S. Provisional Application No. 61/887,969, filed Oct. 7, 2013, entitled "User-Friendly Detection Unit," and claims priority to U.S. Provisional Application No. 61/887,963, filed Oct. 7, 2013 which are each hereby incorporated by reference for all purposes.

BACKGROUND

A conventional smoke or carbon monoxide alarm likely provides no indication that a hazardous condition is present until a loud alarm is sounded. Such an arrangement may be annoying to a user when the alarm has been triggered accidentally. For example, a small amount of smoke generated by cooking may be enough to trigger a smoke alarm to sound. The user may then have to remedy the condition that caused the alarm by airing out the room in which the smoke alarm is located to clear the smoke and/or by actuating a button on the alarm to silence it. Further, the user may be left guessing as to whether the remediation actions being taken by the user are sufficient to alleviate the conditions that initially triggered the alarm to sound.

FIELD

This document relates to systems, devices, methods, and related computer program products for smart buildings including the smart home. More particularly, this patent specification relates to detection units, such as hazard detection units (e.g., smoke detectors. carbon monoxide sensors, etc.) or other monitoring devices, that are useful in smart building and smart home environments.

SUMMARY

Methods, systems, devices, apparatuses, and processor-readable mediums are presented for alerting users to easing hazardous conditions. Once a threshold level of a hazardous condition has been realized (e.g., smoke, carbon monoxide), a hazard detector may monitor for the hazardous condition to drop below a (same or different) threshold level. Once the drop occurs an amount of time may be waited. Once a defined time period has elapsed and the hazard condition has not risen above a threshold level, an indication may be output that indicates the hazardous condition is easing. The defined time period may be based on various factors, including the type of hazard, readings from other hazard detectors, and/or a measured humidity level to name only a few examples.

In some embodiments, a method for detecting that a hazardous condition is easing is presented. The method may include measuring, by a hazard detector, a first amount of the hazardous condition present in an ambient environment of the hazard detector. The method may include setting, by the hazard detector, a mode of the hazard detector to a state indicative of the hazardous condition being present in the ambient environment of the hazard detector. The method may include measuring, by a hazard detector, a second amount of the hazardous condition present in the ambient environment of the hazard detector, the second amount of the hazardous condition being less than the first amount of the hazardous condition. The method may include determining, by the hazard detector, that the second amount of the hazardous condition present in the ambient environment of the hazard detector is below a threshold hazardous condition level while the mode of the hazard detector is set to the state indicative of the hazardous condition being present. The method may include tracking, by the hazard detector, a time period during which the amount of the hazardous condition present in the ambient environment of the hazard detector has remained below the threshold hazardous condition level while the mode of the hazard detector is set to the state indicative of the hazardous condition being present. The method may include determining, by the hazard detector, that the time period has reached at least a threshold duration, during such time period the amount of the hazardous condition present in the ambient environment of the hazard detector having remained below the threshold hazardous condition level while the mode of the hazard detector is set to the state indicative of the hazardous condition being present. The method may include outputting, by the hazard detector, an indication of the hazardous condition easing in response to the time period being at least the threshold duration.

Such embodiments may include one or more of the following features: An auditory indication may be output that comprises a spoken message indicative of the hazardous condition easing. The spoken message indicative of the hazardous condition easing may include a spoken indication of a name of a room in which the hazardous condition is easing. The method may include setting, by the hazard detector, the mode of the hazard detector to a second state indicative of the hazardous condition not being present in the ambient environment of the hazard detector in response to determining that the time period has reached at least the threshold duration. The method may include determining, by the hazard detector, the threshold duration based on a type of the hazardous condition. The hazardous condition may be selected from the group consisting of: smoke and carbon monoxide. The threshold duration may vary based on whether the hazardous condition is smoke or carbon monoxide. The method may include determining, by the hazard detector, one or more event characteristics of the hazardous condition. The method may include determining, by the hazard detector, the threshold duration based on the one or more event characteristics of the hazardous condition. The method may include receiving, by the hazard detector, from one or more hazard detectors located in other rooms of a structure in which the hazard detector is installed, information indicative of the hazardous condition. The method may include determining, by the hazard detector, the threshold duration based on the received information indicative of the hazardous condition from the one or more hazard detectors located in other rooms of the structure in which the hazard detector is installed. The method may include measuring, by the hazard detector, a humidity level in the ambient environment of the hazard detector. The method may include determining, by the hazard detector, the threshold duration based on the measured humidity level. The method may include sounding, by the hazard detector, an auditory alarm, indicative of the hazardous condition being present in the ambient environment of the hazard detector.

In some embodiments, a non-transitory processor-readable medium for a hazard detector is presented. The medium may include processor-readable instructions configured to cause one or more processors of the hazard detector to perform any or all of the above steps detailed in relation to the methods.

In some embodiments, a hazard detector is presented. The hazard detector may include a hazard sensor that measures amounts of a hazardous condition present in an ambient environment of the hazard detector. The hazard detector may include an output device that outputs information into the ambient environment of the hazard detector. The hazard detector may include a processing system that comprises one or more processors, the processing system being in communication with the output device and the hazard sensor. The processing system may be configured to receive a first measurement of the first amount of the hazard present in the ambient environment of the hazard detector. The processing system may be configured to set a mode of the hazard detector to a state indicative of a hazardous condition being present in the ambient environment of the hazard detector. The processing system may be configured to receive a second measurement of a second amount of the hazardous condition present in the ambient environment of the hazard detector, the second amount of the hazardous condition being less than the first amount of the hazardous condition. The processing system may be configured to determine that the second amount of the hazardous condition present in the ambient environment of the hazard detector is below a threshold hazardous condition level while the mode of the hazard detector is set to the state indicative of the hazardous condition being present. The processing system may be configured to track a time period during which the amount of the hazardous condition present in the ambient environment of the hazard detector has remained below the threshold hazardous condition level while the mode of the hazard detector is set to the state indicative of the hazardous condition being present. The processing system may be configured to determine that the time period has reached at least a threshold duration, during such time period the amount of the hazardous condition present in the ambient environment of the hazard detector having remained below the threshold hazardous condition level while the mode of the hazard detector is set to the state indicative of the hazardous condition being present. The processing system may be configured to cause the output device to output an indication of the hazardous condition easing in response to the time period being at least the threshold duration.

In some embodiments, a hazard detector apparatus is presented. The apparatus may include means for measuring a first amount of the hazardous condition present in an ambient environment of the hazard detector. The apparatus may include means for setting, a mode of the hazard detector to a state indicative of the hazardous condition being present in the ambient environment of the hazard detector. The apparatus may include means for measuring a second amount of the hazardous condition present in the ambient environment of the hazard detector, the second amount of the hazardous condition being less than the first amount of the hazardous condition. The apparatus may include means for determining that the second amount of the hazardous condition present in the ambient environment of the hazard detector apparatus is below a threshold hazardous condition level while the mode of the hazard detector is set to the state indicative of the hazardous condition being present. The apparatus may include means for tracking a time period during which the amount of the hazardous condition present in the ambient environment of the hazard detector apparatus has remained below the threshold hazardous condition level while the mode of the hazard detector is set to the state indicative of the hazardous condition being present. The apparatus may include means for determining that the time period has reached at least a threshold duration, during such time period the amount of the hazardous condition present in the ambient environment of the hazard detector having remained below the threshold hazardous condition level while the mode of the hazard detector is set to the state indicative of the hazardous condition being present. The apparatus may include means for outputting an indication of the hazardous condition easing in response to the time period being at least the threshold duration.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIGS. 12-18 represent various illumination states and audio messages that may be output by a hazard detector.

FIG. 19 illustrates a chart indicative of various situations in which pre-alert messages and sounds may be silenced and situations in which messages and sounds cannot be silenced.

DETAILED DESCRIPTION

Conventional hazard alarms typically make a loud noise when a hazardous condition, such as smoke or carbon monoxide, is detected. Oftentimes, the hazardous condition is not dangerous enough for a user to abandon the structure. Rather, the user may take steps to ameliorate the hazardous condition. For instance, if the user burned food on a stove, the user may open a window and turn on a fan or wave a towel to circulate air. As another example, if a small fire has started, the user may douse it with water. A conventional hazard alarm may continue making noise until the hazardous condition is no longer detected or the user pushes a button on the alarm to silence the alarm.

Rather than having a hazard detector have only binary states (i.e., alarm on or off), embodiments detailed herein describe hazard detectors that can inform users of not only when a hazardous condition is present, but when that hazardous condition is rising and/or easing. Such information may be useful to a user in deciding whether to evacuate a structure and/or in determining if steps the user has taken to ameliorate the hazard are helping to dissipate the hazardous condition.

When embodiments of a hazard detector as detailed herein make an announcement (which may involve sound and/or light) as to a hazardous condition easing, various factors may be evaluated to determine when such an announcement should be made, including: the type of hazard, the humidity, characteristics of the detected hazard, and/or the number of hazard detectors that have detected the hazardous condition. Other factors are also possible. Based on such factors, the hazard detector may determine if the hazard has been easing for a sufficient period of time to announce that the hazardous condition appears to be decreasing or has dissipated completed.

Further, the ability to inform a user that a hazardous condition is easing may be used in conjunction with a multi-state hazard detector. Rather than having the hazard detector have only two alarm states, such as alarm and non-alarm, a hazard detector may have three or more states: non-alarm (in which the hazard detector monitors the ambient environment for hazards), pre-alarm (the hazard detector detects a small amount of a hazard, the amount of the hazard being insufficient to sound the full alarm), and alarm (the hazard detector's alarm sounding for a greater amount of the hazard being detected). Such a pre-alarm state may inform a user that the alarm is going to sound soon if the hazardous condition keeps getting worse. Such a pre-alarm state may allow a user time to ameliorate the hazardous condition before having a full alarm sound. When the state of the hazard detector is downgraded, an announcement as to the easing of the hazardous condition may be made.

Figure 1:
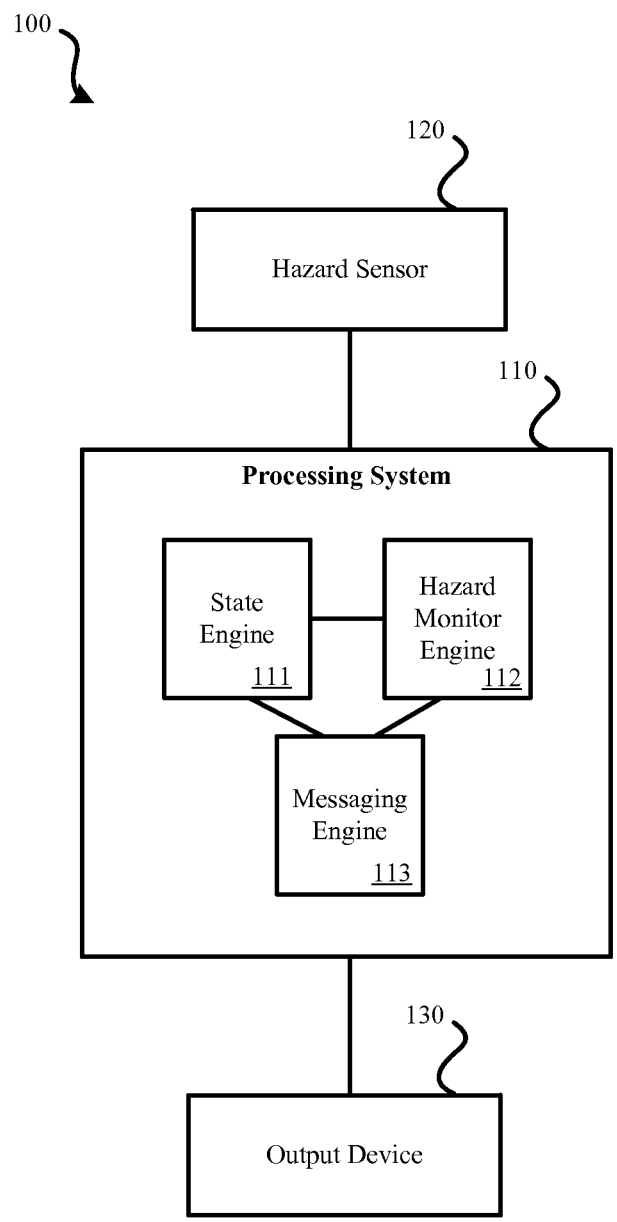
FIG. 1 illustrates an embodiment of a hazard detector for detecting an easing of a hazardous condition.

FIG. 1 illustrates an embodiment of a hazard detector 100 that can detect an easing of a hazardous condition. Hazard detector 100 may include: processing system 110, hazard sensor 120, and output device 130. Processing system 110 may include one or more processors that execute various modules. Such modules may be implemented using software or firmware. Alternatively, such modules may be implemented directly as special-purpose hardware. Processing system 110 may include two processors. One processor may serve as a low-level processor that handles safety-critical tasks, such as receiving data from hazard sensor 120 and sounding an alarm when the hazard reaches a threshold amount. Another processor may serve as a high-level processor that handles usability functionality, such as providing a user with spoken messages, detecting gestures, and communicating with a wireless network. These processors may communicate with each other and other components of hazard detector 100 to function as processing system 110. In some embodiments, the low-level processor may be capable of functioning independently of the high-level processor. For example, if the high-level processor becomes non-functional, the low-level processor may still be able to sound an alarm if a hazard is detected.

Hazard sensor 120 may detect one or more types of hazards. Hazard sensor 120 may detect smoke (as a signal that fire is present) or carbon monoxide, as two examples. Hazard sensor 120 may provide processing system 110 with an indication of an amount of a hazard detected in the ambient environment of hazard detector 100. Processing system 110 may be configured to analyze the indication of the amount of the hazard detected by hazard sensor 120.

Hazard monitor engine 112 of processing system 110 may receive indications of the amount of a hazard detected in the ambient environment of hazard detector 100 from hazard sensor 120. Hazard detector 100 may be configured to be set into multiple states, such as detailed in relation to FIGS. 3A-3C. Based upon the comparison to one or more threshold values, hazard monitor engine 112 may provide input to state engine 111, which may track which state hazard detector 100 is currently in. For instance, when a first threshold value is exceeded, state engine 111 may be set to a pre-alarm state. If a second threshold value of detected hazard is exceeded, state engine 111 may be set to an alarm state.

Hazard monitor engine 112 and state engine 111 may be in communication with messaging engine 113. Messaging engine 113 may determine one or more auditory and/or visual messages to be output to a user based upon input from state engine 111 and/or hazard monitor engine 112. For instance, when messaging engine 113 determines that the state of hazard detector 100 has entered a pre-alarm state, messaging engine 113 may cause output device 130 to provide an auditory and/or visual indication to a user that the amount of a hazard in the environment is rising. When messaging engine 113 determines that the state of hazard detector 100 has exited an alarm state or a pre-alarm state, messaging engine 113 may cause output device 130 to provide an auditory and/or visual announcement to a user that the amount of a hazard in the environment is easing.

Output device 130 may be configured to output light or sound into the ambient environment of the hazard detector. Output device 130 may be a speaker that is capable of outputting human speech. Output device 130 may alternatively be one or more lights that can output one or more colors and one or more animation patterns. In some embodiments, multiple output devices are present, such as to output light and sound to indicate a pre-alarm state, an alarm state, and/or when a hazardous condition has eased.

Figure 2:
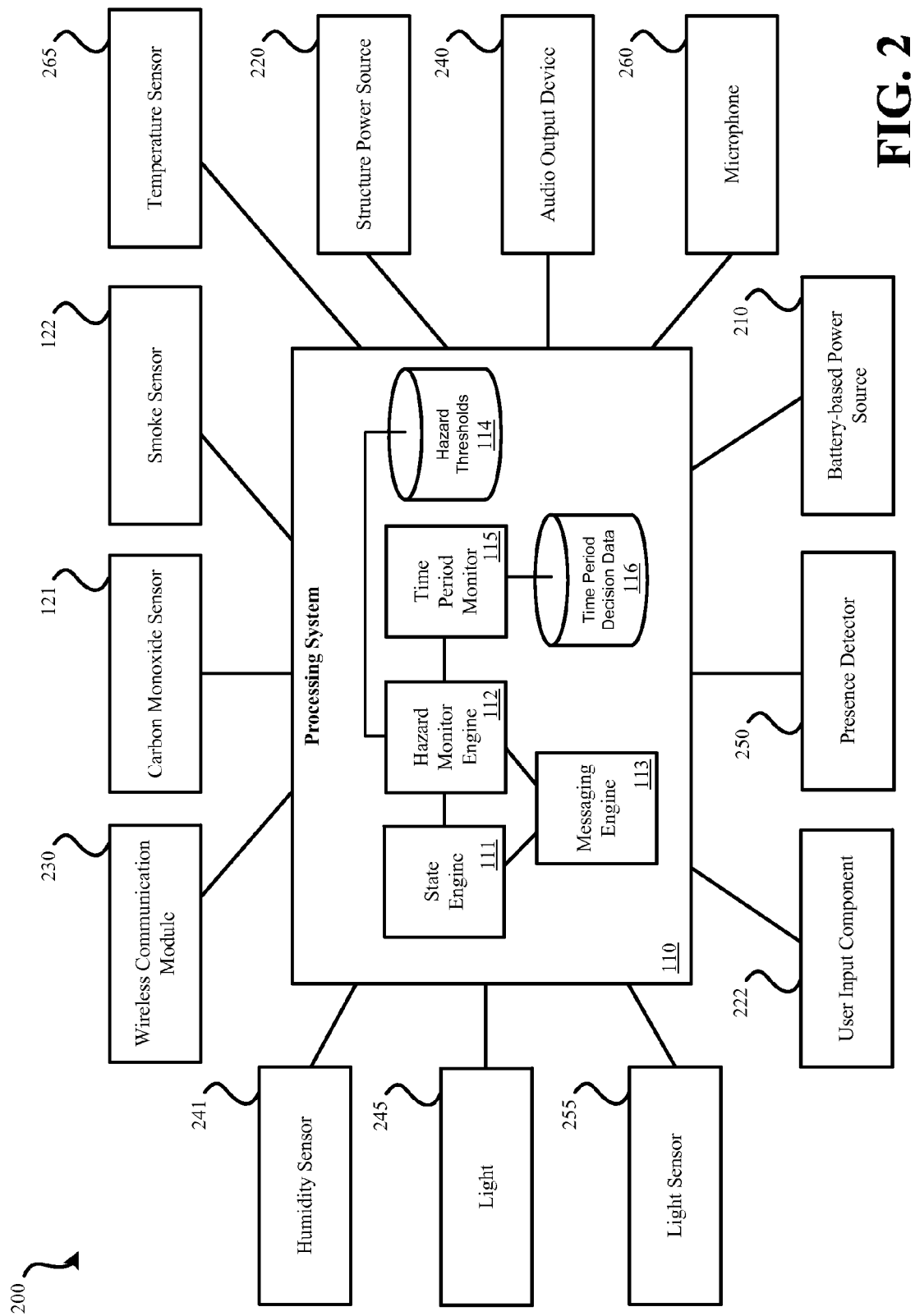
FIG. 2 illustrates an embodiment of another hazard detector for detecting an easing of a hazardous condition.

FIG. 1 illustrates a simplified embodiment of hazard detector 100. It should be understood that multiple hazard sensors and/or multiple output devices may be present in other embodiments. For example, FIG. 2 illustrates an embodiment of hazard detector 200 for detecting an easing of a hazardous condition. Hazard detector 200 represents a more detailed embodiment that includes a greater number of components and modules. In hazard detector 200, various components may be present including: processing system 110, light sensor 255, light 245, carbon monoxide sensor 121, smoke sensor 122, battery-based power source 210, wireless communication module 230, user input component 222, structure power source 220, presence detector 250, microphone 260, audio output device 240, humidity sensor 241, and temperature sensor 265.

Processing system 110 of hazard detector 200 may include multiple submodules. Such submodules may be implemented using hardware, firmware, and/or software that is executed by underlying hardware, such as one or more processors. Such modules may include: state engine 111, hazard monitor engine 112, messaging engine 113, hazard thresholds 114, time period monitor 115, and time period decision data 116. For instance, such modules may represent code that is executed by a high-level processor and/or a low-level of hazard detector 200.

Hazard monitor engine 112 may receive indications of the amount of a hazard detected in the ambient environment of hazard detector 200 from carbon monoxide sensor 121 and smoke sensor 122. State engine 111 of hazard detector 200 may be configured to be set into multiple states, such as detailed in relation to FIGS. 3A-3C. Based upon the comparison to one or more threshold values from hazard thresholds 114, hazard monitor engine 112 may provide input to state engine 111 and/or messaging engine 113.

Hazard monitor engine 112 and state engine 111 may be in communication with messaging engine 113. Messaging engine 113 may determine one or more auditory and/or visual messages to be output to a user based upon input from state engine 111 and/or hazard monitor engine 112. For instance, when messaging engine 113 determines that the state of hazard detector 100 has entered a pre-alarm state, messaging engine 113 may cause output device 130 to provide an auditory and/or visual indication to a user that the amount of a hazard in the environment is rising. When messaging engine 113 determines that the state of hazard detector 100 has exited an alarm state or a pre-alarm state, messaging engine 113 may cause output device 130 to provide an auditory and/or visual indication to a user that the amount of a hazard in the environment is easing.

Hazard monitor engine 112 may compare the received levels of a hazard to threshold values of stored hazard thresholds 114. A first threshold value may be defined to determine when state engine 111 should be placed into a pre-alarm mode. A second threshold value may be defined to determine when state engine 111 should be placed into an alarm mode. A third threshold value may be defined to determine when state engine 111 should be returned from the alarm mode to the pre-alarm mode or to a non-alarm mode and/or to determine when the hazardous condition is easing. Such thresholds present in hazard thresholds 114 may be selected based on the type of hazard and/or other conditions.

Time period monitor 115 may be used in conjunction with hazard monitor engine 112 to determine when the state maintained by state engine 111 should be decreased from an alarm mode to a pre-alarm mode or to a non-alarm mode and/or when an announcement should be made that the hazardous condition is easing. For instance, it may be required that the amount of the hazard detected in the environment of hazard detector 200 remain below a threshold amount stored by hazard thresholds 114 for at least a period of time before the state of the hazard detector is downgraded. The period of time may vary based on multiple factors, such as the type of hazard, the number of hazard detectors that detected the hazard, characteristics of the hazard, and/or humidity level detected by hazard detector 200. Time period monitor 115 may monitor an amount of time for which the detected hazard level as received by hazard monitor engine 112 has remained below a threshold defined in stored hazard thresholds 114. Time period monitor 115 may also determine the duration of the period of time by accessing time period decision data 116 and assessing one or more factors associated with the hazard. For instance, time period monitor 115 may retrieve a predefined duration for the period of time from time period decision data 116 based on the type of hazard. This predefined duration may be adjusted based on various parameters such as the humidity level in the ambient environment of hazard detector 200. Time period decision data 116 may contain indications of how the period of time should be lengthened if the hazard has been detected by multiple hazard detectors located within a structure in which hazard detector 200 is installed. Further, time period decision data 116 may store information indicative of how long the detected level of hazard is required to be below the threshold value based on characteristics of the detected hazard. For instance, the level of detected hazard having increased rapidly may result in a different period of time than if the level of detected hazard increased slowly. Based upon analyzing the detected level of hazard in the environment and time period decision data 116, time period monitor 115 may determine when state engine 111 should downgrade its state from alarm or pre-alarm. Messaging engine 113 may output an indication that the hazardous condition is easing based upon the state of state engine 111 being downgraded or time period monitor 115 directly informing messaging engine 113 that an indication of the condition easing should be output.

Light sensor 255 detects the presence of light in the ambient environment of hazard detector 100. Light sensor 255 may detect a brightness level in the ambient environment of hazard detector 200. Such a brightness level may be affected by natural and artificial lighting. Light sensor 255 may provide an indication of the brightness level in the ambient environment of hazard detector 200 to processing system 110. Light 245 may represent a light integrated into hazard detector 200 that outputs light to the external environment around hazard detector 200. Light 245 may be controlled by processing system 110. Light 245 may include one or more lighting elements, such as light emitting diodes (LEDs). Light 245 may be capable of outputting various illumination modes that can include: multiple colors, multiple animation patterns, and/or such multiple animation patterns at varying speeds. The at least one color, animation pattern, and speed of animation output by light 245 may be determined based on a determination performed by processing system 110. Therefore, based on conditions monitored by processing system 110, light 245 may be illuminated or disabled. When light 245 is illuminated, the one or more colors, animation pattern, and/or speed of the animation output by light 245 may vary based on a determination performed by processing system 110.

Presence detector 250 may detect a presence or motion within the ambient environment of hazard detector 200. Presence detector 250 may include one or more passive infrared (PIR) sensors and/or ultrasonic sensors that receive infrared radiation (or reflected ultrasonic sound) from the ambient environment of the hazard detector. For instance, a user walking or otherwise moving in the vicinity of hazard detector 200 emits infrared radiation which may be detected by presence detector 250. In other embodiments, presence detector 250 may use some other form of sensor than a PIR sensor. Presence detector 250 may provide an indication to processing system 110 of when motion is present in the ambient environment of hazard detector 200. More generally, presence detector 250 may be a form of sensor that can detect a user's presence even if motionless. In some embodiments, presence detector 250 outputs raw data that is analyzed by processing system 110 to determine if motion is present or a user is otherwise present. In some embodiments, motion may be analyzed to determine if it likely corresponds to a person or is incidental (e.g., a pet, an object being warmed by sunlight, etc.).

In hazard detector 200, two hazard sensors are present: carbon monoxide sensor 121 and smoke sensor 122. In some embodiments, multiple versions of each of these types of sensors can be present. For instance, an ionization and a photoelectric smoke sensor may be present in hazard detector 200. When carbon monoxide sensor 121 senses carbon monoxide or smoke sensor 122 senses smoke, indication may be sent to a processor of processing system 110. An indication of an alarm condition may be transmitted to a low-level processor that triggers an alarm to sound and/or a light color and/or animation to be output by light 245. This low-level processor may trigger light 245 directly to illuminate in a state indicative of a hazard or may provide input to a high-level processor that is part of processing system 110 that triggers a lookup of an illumination definition to determine an appropriate color, animation, and/or speed of animation to use for illumination of light 245. Regardless of whether the high-level or low-level processor is used, a different color, animation, and/or speed may be used for carbon monoxide as compared to smoke. In some embodiments, both the low and high level processors are capable of causing light 245 to illuminate.

Wireless communication module 230 may allow processing system 110 to communicate with a wireless network present within the structure in which hazard detector 200 is installed. For instance, wireless communication module 230 may communicate with a wireless network that uses the IEEE 802.11a/b/g network protocol standard for communication. Wireless communication module 230 may permit processing system 110 to communicate with a remote server, which may be maintained by a manufacturer of hazard detector 200 or by a third-party. The remote server may be configured to provide information to processing system 110 about an account of a user associated with hazard detector 200. For instance, if an account of the user maintained at the remote server requires attention from a user, such indication may be provided to processing system 110 via wireless communication module 230. Such indication may be provided by the remote server in response to inquiry from processing system 110 made to the remote server. Further, processing system 110 may transmit status information to a remote server. Such an arrangement may permit a user to view status information about the hazard detector by logging in to the remote server via a computing device and accessing the user account.

Wireless communication module 230 may also permit direct connection with a wireless computerized device. For instance, wireless communication module 230 may create a wireless area network (e.g., WiFi network) that a computerized wireless device, such as a tablet computer or smartphone, can connect with. Once connected, messages may be exchanged between processing system 110 (via wireless communication module 230) and a wireless computerized device, such as to permit an initial configuration of hazard detector 200 to be performed via the computerized wireless device. In other embodiments, such an initial configuration is performed via a network connection through a router or other form of direct communication, such as Bluetooth® or WiFi Direct®.

Wireless communication module 230 may also allow for communication with one or more other hazard detectors installed within the same structure as hazard detector 200. For instance, hazard detectors may be installed within various rooms within a structure. Each hazard detector may store an indication of the type of room it is installed within. These hazard detectors may be configured to alert each other when a hazard is detected. As such, while a hazard may be detected by another hazard detector, hazard detector 200 may alert a user to the presence of the hazard in the other room. When a hazard is present, hazard detector 200 may receive indications from other hazard detectors indicative of whether that hazard detector is also sensing the hazard. Hazard detectors that are not sensing the hazard may not provide such an indication or may transmit a message indicative of the hazard not being detected.

User input component 222 may represent a component that receives input that can be passed to processing system 110. User input component 222 may take the form of a button or switch on hazard detector 200. By depressing the button or otherwise actuating user input component 222, a user can provide input via user input component 222 to processing system 110. For instance, user input component 222 may be used by a user to disable an alarm being sounded by hazard detector 200. User input component 222 may be encircled or have its perimeter otherwise outlined by light 245 (that is, by the light itself and/or by light output by light 140). Therefore, when light 245 is active, and the user desires to provide input (e.g., to silence an alarm), the user may touch or push hazard detector 200 within the area defined by light 245 and/or the light output by light 245.

Hazard detector 200 may include battery-based power source 210 and structure power source 220. Structure power source 220 may be used to power hazard detector 200 when such power is available. Structure power source 220 may represent a hard-wired connection within a structure (e.g., house, building, office, etc.) that provides an AC or DC power to one or more hazard detectors located throughout the structure. While the AC or DC power may be available a significant percentage of time (e.g., 99.5% of the time), it may be desirable for hazard detector 200 to continue functioning if structure power is unavailable (e.g., during a power failure). As such, battery-based power source 210 may also be present. Battery-based power source 210 may include one or more batteries which power the various components of hazard detector 200 when structure power source 220 is not available. In some embodiments of hazard detector 200, structure power source 220 is not present and/or the hazard detector may not be capable of connected with structure power source 220. As such, hazard detector 200 may permanently rely on battery-based power source 210 to power components of hazard detector 200. Structure power source 220 and battery-based power source 210 are illustrated in FIG. 2 as connected with processing system 110. It should be understood that, while structure power source 220 and battery-based power source 210 are illustrated as only connected with processing system 110, this is for simplicity of illustration only; structure power source 220 and/or battery-based power source 210 may be connected to the various components of hazard detector 200 as necessary to power such components.

Audio output device 240 and light 245 may represent different forms of output device 130 of hazard detector 100. Audio output device 240 may be a speaker that is configured to output sound. Audio output device 240 may be capable of outputting synthesized or recorded speech, thus allowing spoken messages to be output to users in the vicinity of hazard detector 200. Audio output device 240 may receive vocal messages to be output from messaging engine 113.

Other sounds, such as an alarm buzzing or ringing may also be generated by audio output device 240. Audio output device 240 may include a piezo sound generator configured to generate a very loud alarm sound.

Humidity sensor 241 may detect humidity level in the ambient environment of hazard detector 200. An indication of the detected humidity level may be provided to processing system 110. This humidity level may be used to determine the time period for which the detected level of hazard is required to be below a threshold value before the state of hazard detector 200 is downgraded and/or an announcement is made that the hazardous condition has eased. Microphone 260 may be used to detect sound the vicinity of hazard detector 200. For instance, spoken commands by user may be received by microphone 260 and processed by processing system 110.

Temperature sensor 265 may be used by hazard detector 200 to monitor the ambient temperature of hazard detector 200. Temperature measurements made by temperature sensor 265 may be used in controlling when HVAC systems are turned on or off.

Figure 3A:
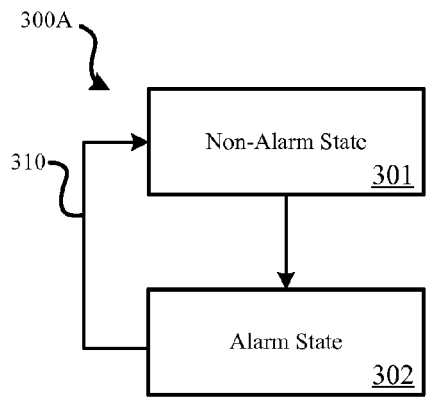
FIGS. 3A, 3B, and 3C illustrate embodiments of various state flows of a hazard detector that detects an easing of a hazardous condition.
Figure 3B:
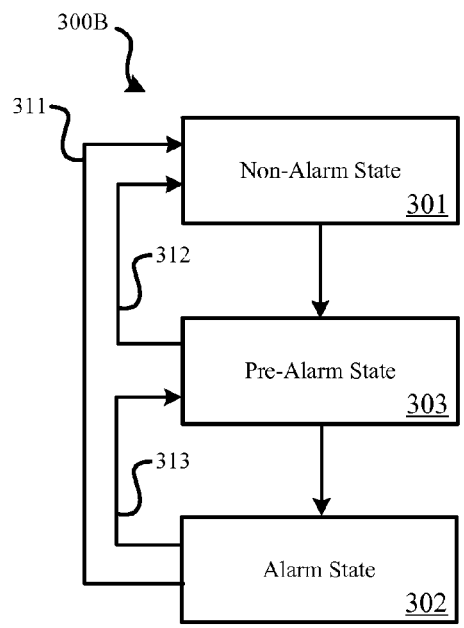
Figure 3C:
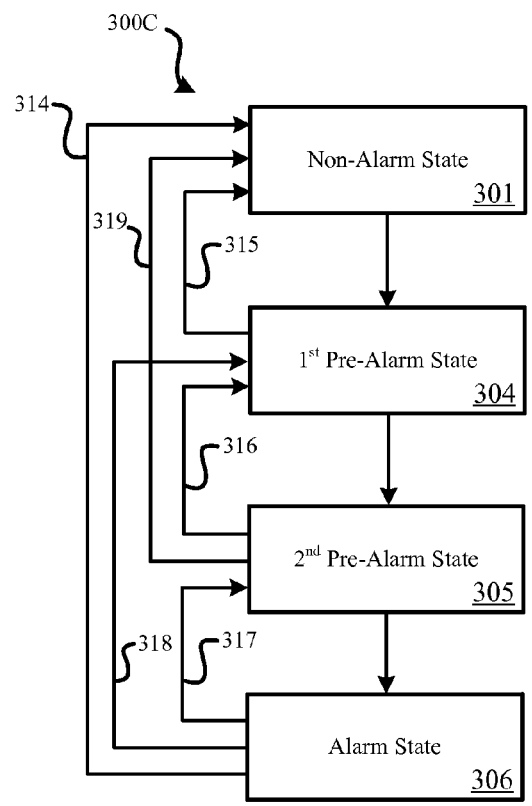

FIGS. 3A, 3B, and 3C illustrate embodiments of various state flows of a hazard detector that detects an easing of a hazardous condition. State flows 300A, 300B, and 300C may be implemented on hazard detector 100, hazard detector 200, or some other embodiment of a hazard detector. FIG. 3A illustrates a state flow 300A of a hazard detector that has two states: non-alarm state 301 and alarm state 302. Non-alarm state 301 may also be referred to as a standby or monitor mode. In non-alarm state 301, the presence of a hazard may be monitored for. In non-alarm state 301, no alarm may be sounded nor may a light be illuminated to be indicative of an alarm. In alarm state 302, an auditory and/or visual alarm may be sounded and/or illuminated, respectively, by the hazard detector. The level of hazard detected in the environment of the hazard detector may continue to be monitored. If the level decreases below a defined threshold amount, flow 310 may be followed to downgrade the state of the hazard detector back to the non-alarm state 301.

Flow 310 occurring may result in the hazard detector outputting an indication that the hazardous condition is easing. In some embodiments, in addition to the level of detected hazard falling below a threshold, the level of detected hazard may be required to remain below the threshold for predefined period of time, which may vary based on several factors, before flow 310 is followed and then indication of the hazardous condition easing being output by the hazard detector. In some embodiments, flow 310 results in a synthesized spoken message being output by hazard detector that indicates, for example: "[Type of Hazard] is easing." The [Type of Hazard] may vary based on if smoke or carbon monoxide was detected. As another example, the hazard detector may indicate the room in which the hazard detector is located. For example, the hazard detector may output: "[Type of Hazard] is easing in the [room]." A user may have previously provided the hazard detector with room designation in which the hazard detector is installed, such as a bedroom, kitchen, bathroom, etc.

FIG. 3B illustrates a state flow 300B of a hazard detector that has three states: non-alarm state 301, alarm state 302, and pre-alarm state 303. Generally, pre-alarm states and alarm states can be referred to as states indicative of a presence of a hazardous condition (albeit in different amounts). In non-alarm state 301, the presence of a hazard may be monitored for. In non-alarm state 301, no alarm may be sounded nor may a light be illuminated to be indicative of an alarm. If an amount of hazard is detected that exceeds a first threshold, the state of the hazard detector is upgraded to pre-alarm state 303. In pre-alarm state 303, the full alarm of the hazard detector may not sound. However, a message, such as a spoken message, may be output to a user that indicates that a level of hazard in the environment has risen or is rising. In some embodiments, recommendations may be made to the user as to how to deal with the rising level of the hazard. In some embodiments, a light of the hazard detector may be illuminated to indicate the pre-alarm state.

If the level of hazard detected in the ambient environment of the hazard detector decreases, such as below the first threshold amount or below some other defined threshold amount, flow 312 may be followed to downgrade the state of the hazard detector from pre-alarm state 303 to non-alarm state 301. Flow 312 may result in a message being output by the hazard detector that is indicative of the hazardous condition easing. If the level of hazard detected in the ambient environment of the hazard detector increases, such as above a second threshold amount (greater than the first threshold amount), pre-alarm state 303 may be upgraded to alarm state 302. In alarm state 302, an auditory and/or visual alarm may be sounded and/or illuminated, respectively, by the hazard detector. The amount of hazard detected in the environment of the hazard detector may continue to be monitored.

If the amount of hazard decreases below the second threshold amount (or some other defined threshold amount), flow 313 may be followed to downgrade the state of the hazard detector back to pre-alarm state 303. Alternatively, flow 311 may be followed to downgrade the state of the hazard detector from alarm state 302 to non-alarm state 301. Based on either flow 311 or flow 313 occurring, the message may be output by the hazard detector that indicates that the hazard condition is easing. Whether flow 313 or 311 is followed may depend on how much the level of detected hazard has fallen in the ambient environment of the hazard detector. In some embodiments, only flows 312 and 313 are available for downgrading the state of the hazard detector. In other embodiments, only flows 311 and 312 are available for downgrading the state of the hazard detector. A message being output to a user indicative of the hazardous condition easing may be assigned to any or all of flows 311, 312, 313. For instance, for flow 313, a message may indicate that the hazardous condition has started to ease, while a message for flow 312 may indicate that the hazardous condition has eased further.

As with state flow 300A, in addition to the detected level of hazard being required to fall below one or more threshold amounts in order for the state of the hazard detector to be downgraded, the detected level of hazard may be required to stay below the threshold amount for at least a period of time prior to the state of the hazard detector being downgraded. This period of time may be determined based on one or more factors, as discussed in relation to method 600 of FIG. 6.

FIG. 3C illustrates a state flow 300C of a hazard detector that has four states: non-alarm state 301, alarm state 302, first pre-alarm state 304, and second pre-alarm state 305. In non-alarm state 301, the presence of hazards may be monitored for. In non-alarm state 301, no alarm may be sounded nor may a light be illuminated to be indicative of an alarm. If an amount of hazard is detected that exceeds a first threshold, the state of the hazard detector is upgraded to first pre-alarm state 304. In first pre-alarm state 304, the full alarm of the hazard detector may not sound nor be lit. However, a message, such as a spoken message, may be output to a user that indicates that a level of hazard in the environment is rising. In some embodiments, recommendations may be made to the user as to how to deal with the rising level of the hazard. In some embodiments, a light of the hazard detector may be illuminated to indicate the first pre-alarm state 304.

If the level of hazard detected in the ambient environment of the hazard detector decreases, such as below the first threshold amount or below some other defined threshold amount, flow 315 may be followed to downgrade the state of the hazard detector from first pre-alarm state 304 to non-alarm state 301. Flow 315 may result in a message being output by the hazard detector that is indicative of the hazardous condition easing. If the level of hazard detected in the ambient environment of the hazard detector increases, such as above a second threshold amount, first pre-alarm state 304 may be upgraded to second pre-alarm state 305. In second pre-alarm state 305, the full alarm of the hazard detector may still not sound nor be lit. However, a message, such as a spoken synthesized or recorded message, may be output to a user that indicates that a level of hazard in the environment is still rising. This message may be more urgent than the message associated with first pre-alarm state 304. In some embodiments, recommendations may be made to the user as to how to deal with the continued rising level of the hazard. In some embodiments, a light of the hazard detector may be illuminated to indicate the second pre-alarm state 305.

If the detected hazard level increases above a third threshold amount, second pre-alarm state 305 may be upgraded to alarm state 306. In alarm state 302, an auditory and/or visual alarm may be sounded and/or illuminated, respectively, by the hazard detector. The level of hazard detected in the environment of the hazard detector may continue to be monitored.

Flows 314, 315, 316, 317, 318, and 319 represent various flows of a state of the hazard detector being downgraded. In some embodiments, when the detected level of a hazard drops below a threshold value, the hazard detector may be downgraded to the non-alarm state 301. In other embodiments, the hazard detector may downgrade its state through one or more pre-alarm states based on the detected hazard level being less than one or more threshold amounts. For instance, as the detected hazard level in the ambient environment of the hazard detector decreases, alarm state 306 may be downgraded to second pre-alarm state 305 according to flow 317, second pre-alarm state 305 may be downgraded to first pre-alarm state 304 following flow 316 and first pre-alarm state 304 may be downgraded to non-alarm state 301 via flow 315. Further, depending on the detected level of hazard, various states may be skipped. For instance, alarm state 306 may be downgraded to first pre-alarm state 304 via flow 318. Similarly, second pre-alarm state 305 may be downgraded to non-alarm state 301 via flow 319. Alarm state 306 may also be downgraded directly to non-alarm state 301 via flow 314.

The threshold values used to determine when to downgrade states of the hazard detector may be the same threshold values used to determine when states of the hazard detector are upgraded. For instance, a same threshold value may be used to determine when first pre-alarm state 304 should be upgraded to second pre-alarm state 305, as when second pre-alarm state 305 should be downgraded to first pre-alarm state 304. Alternatively, the thresholds used for upgrading and downgrading states may vary from each other. For instance, a first threshold value may be used to determine when first pre-alarm state 304 should be upgraded to second pre-alarm state 305, but a second threshold (smaller in magnitude than the first) may be used to determine when second pre-alarm state 305 should be downgraded to first pre-alarm state 304.

A message being output to indicate that a hazardous condition is easing may be associated with all or any of flows 314, 315, 316, 317, 318, and 319. In some embodiments, it may be desirable for only one easing message to be output, such as when the state of the hazard detectors downgraded to non-alarm state 301. In other embodiments, it may be desirable to indicate that the hazardous condition has started to ease, such as at flow 316 or flow 317 and later be followed by another message indicating that the hazardous condition has further eased such as at flow 315.

As with state flows 300A and 300B, in addition to the detected level of hazard being required to fall below one or more threshold amounts in order for the state of the hazard detector to be downgraded, the detected level of hazard may be required to stay below the threshold amount for at least a period of time prior to the state of the hazard detector being downgraded. This period of time may be determined based on one or more factors, as discussed in relation to method 600 of FIG. 6.

While not illustrated in FIG. 3C, or any of the other state flows, it may be possible for a state to be upgraded and skip one or more other states. For instance, if a high enough level of a hazard is detected, non-alarm state 301 may be upgraded directly to alarm state 306. State flows 300A, 300B, and 300C focus on hazard detectors that have two, three, and four states respectively. It should be understood that in other embodiments, a greater number of states may also be possible. In some embodiments, hazard detectors may have a different number of states depending on the type of hazard detected. For instance, state flow 300A may be used for when carbon monoxide is detected while state flow 300B or 300C may be used for when smoke is detected.

Figure 4:
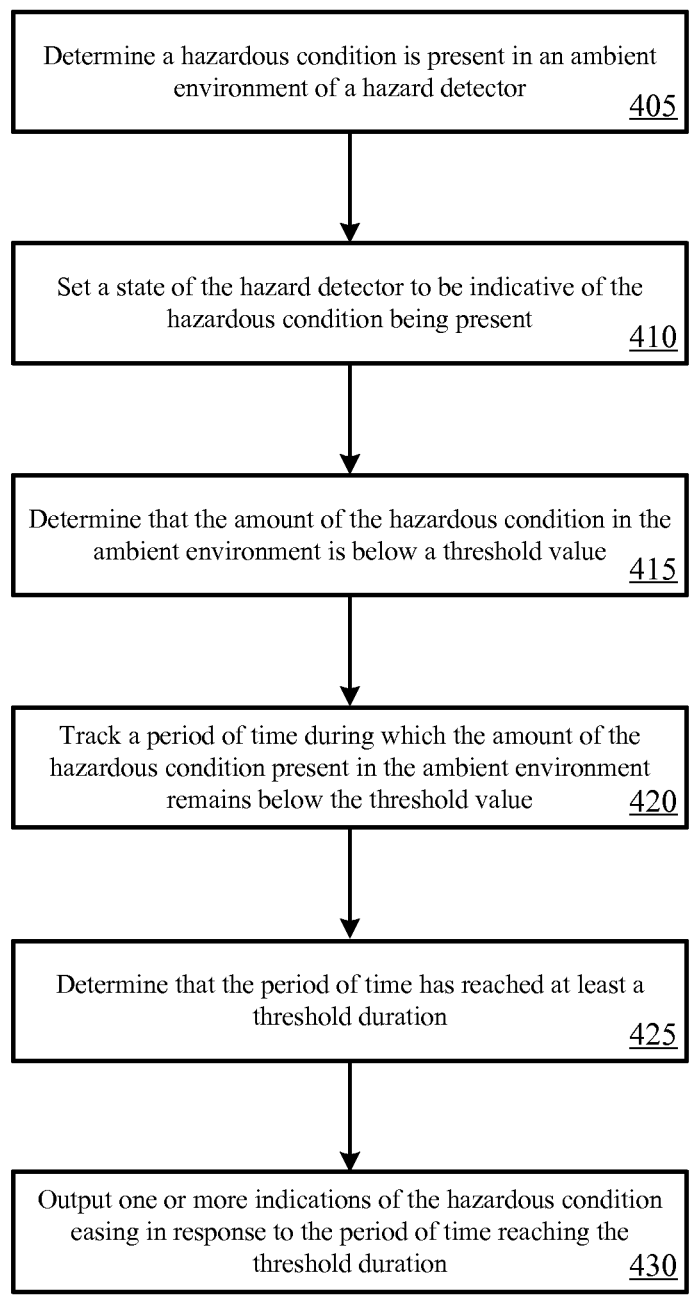
FIG. 4 illustrates an embodiment of a method for detecting an easing of a hazardous condition.

Various methods may be performed by a hazard detector using the states detailed in relation to FIGS. 3A-3C. FIG. 4 illustrates an embodiment of a method 400 for detecting an easing of a hazardous condition. Method 400 may be performed using hazard detector 100, hazard detector 200, or some other embodiment of a hazard detector. Each step of method 400 may generally be performed by a hazard detector. Throughout method 400, one or more sensors of the hazard detector may continue to monitor for and measure amounts of hazardous conditions, such as smoke and/or carbon monoxide, in the ambient environment of the hazard detector.

At step 405, a hazardous condition may be determined to be present in the environment of a hazard detector. Such a determination may be made based on one or more measured amounts of the hazardous condition being compared to a stored threshold value. The hazard may involve the presence of smoke, which can be indicative of fire, carbon monoxide, or some other condition or compound that is potentially dangerous to occupants present in the structure in which the hazard detector is installed. At step 405, the hazard detector may be receiving measurements of the amount of detected hazard in the environment of the hazard detector from one or more sensors of the hazard detector. In response to the threshold value being exceeded by the measured amount of the hazardous condition, method 400 may proceed to step 410. Otherwise, if no amount of the hazardous condition is measured by the hazard detector, the hazard detector may continue to monitor for such a hazardous condition until one is detected.

At step 410, a state of the hazard detector may be set to be indicative of the hazardous condition being present. Referring back to FIGS. 3A-3C, step 410 may involve the hazard detector being set from a non-alarm state to either a pre-alarm state or an alarm state. In indication of the current state of the hazard detector may be stored by the processing system of the hazard detector, such as to a non-transitory storage medium associated with a state engine. While step 410, and later steps of method 400, are being performed, the hazard detector may continue to monitor for hazards in the ambient environment of the hazard detector.

At step 415, the hazard detector may determine that the amount of the hazardous condition in the ambient environment is now below a threshold value. This determination may be based on one or more measurements of hazard level made after step 405 was performed. Therefore, the amount of hazardous condition in the environment of the hazard detector may have decreased since step 405. The threshold used at step 405 to determine that the hazardous condition is present in the ambient environment of the hazard detector may be the same threshold amount used in the analysis of step 415. Alternatively, the threshold values used may differ. For example, the threshold amount used at step 415 may be smaller in magnitude than the threshold amount used to determine that the hazardous condition was present at step 405.

At step 420, following the amount of the hazardous condition being below the threshold, a period of time for which measurements of the hazardous condition has remained below the threshold value may be tracked. If the amount of hazard detected in the ambient environment of the hazard detector exceeds the threshold, the time period may be reset.

Whether an alarm of the hazard detector is sounding during steps 415 and 420 may be dependent on whether the state set at step 410 was a pre-alarm state or an alarm state. If an alarm state, one or more auditory and/or visual alarms may be output by the hazard detector while steps 415 and 420 are being performed. If a pre-alarm state, the hazard detector may be taking no action or may be outputting a warning (pre-alarm message) indicative of the hazard detector being in the pre-alarm state. If a warning (pre-alarm message) is output in the pre-alarm state, the warning will likely be less loud and/or intrusive to a user than auditory and/or visual outputs by the hazard detector in the alarm state. For instance, the warning (pre-alarm message) may be a spoken message that states: "Warning, the hazard level is rising."

At step 425, it may be determined that the period of time which was tracked at step 420 has reached at least a threshold duration. The threshold duration may be stored by the hazard detector. For instance, the threshold duration may be based on the type of hazard. If smoke was determined to be present at step 405, a first threshold duration may be used. If carbon monoxide was determined to be present at step 405, a second threshold duration may be used instead. In some embodiments, rather than a stored threshold duration being defined, the hazard detector may calculate or otherwise modify the threshold duration based on one or more factors, at least some of which are discussed in relation to FIG. 6.

At step 430, the hazard detector may output one or more indications of the hazardous condition easing. The output of step 430 may be performed in response to the period of time being determined to have reached the threshold duration of step 425. The indications of the hazardous condition easing may include: an auditory message, which may include a spoken message, and a visual indication, such as a light of the hazard detector illuminating a color that is not typically associated with a hazard, such as green or blue. Additionally, in response to the period of time having reached at least the threshold duration of step 425, the state of the hazard detector may be downgraded such as in accordance with the embodiments of FIGS. 3A-3C. For example, from an alarm state, the hazard detector may be downgraded to either a non-alarm state or pre-alarm state. If the hazard detector was set to a pre-alarm state at step 410, the hazard detector may be set to a non-alarm state. Further, it is possible in some embodiments that a period of time does not need to be evaluated before an easing announcement is output—rather, the easing announcement is output in response to the level of detected hazard dropping below a threshold amount only.

Figure 5:
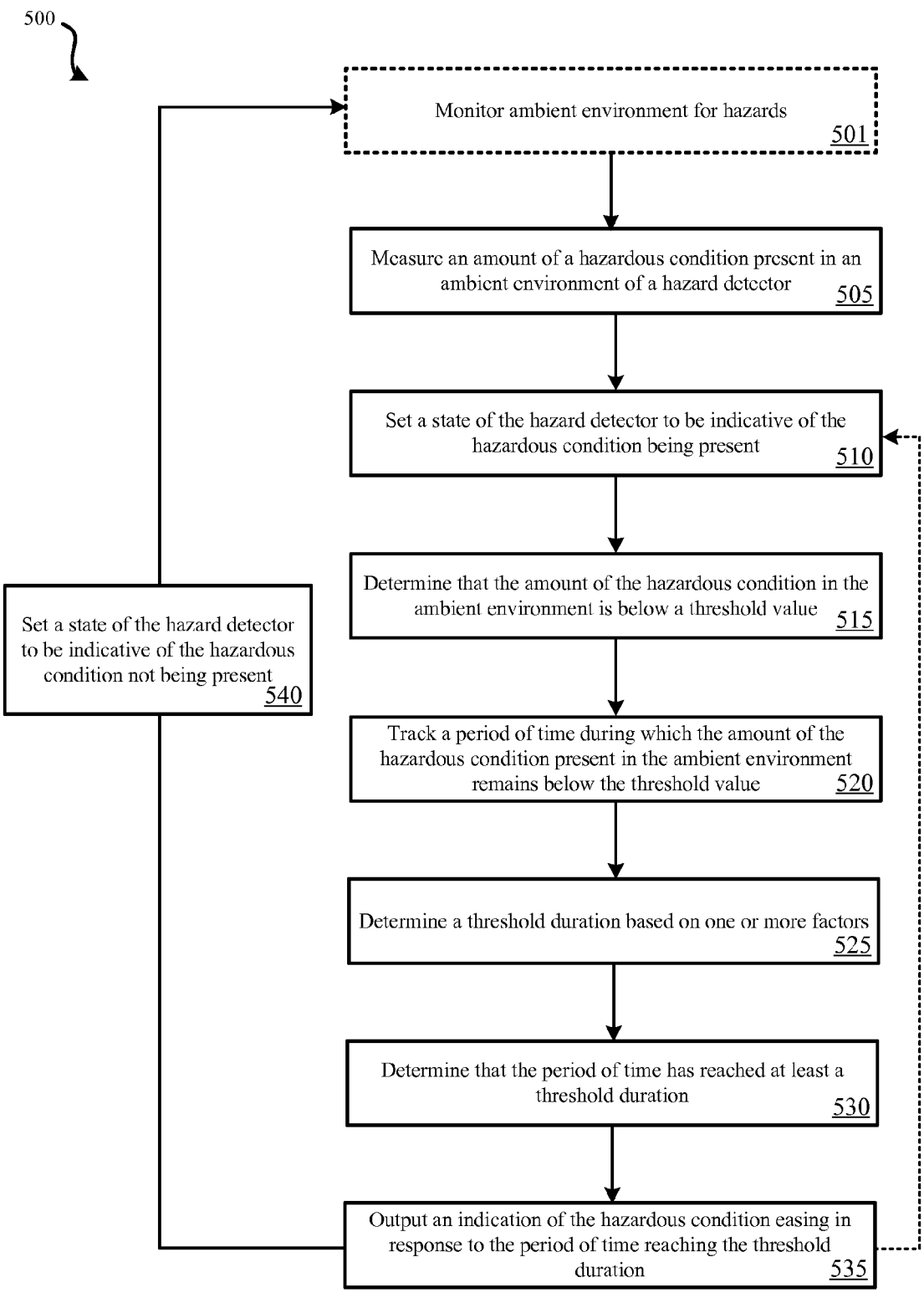
FIG. 5 illustrates an embodiment of a method for detecting an easing of a hazardous condition that varies a time period used in determining when to make an announcement indicating that the hazardous condition has eased.

FIG. 5 illustrates an embodiment of a method 500 for detecting an easing of a hazardous condition that varies a time period used in determining when the hazardous condition has eased. Method 500 may be performed using hazard detector 100, hazard detector 200, or some other embodiment of a hazard detector. Method 500 may represent a more detailed embodiment of method 400. Each step of method 500 may generally be performed by a hazard detector. Throughout method 500, one or more sensors of the hazard detector may continue to monitor for and measure amounts of hazardous conditions, such as smoke and/or carbon monoxide, in the ambient environment of the hazard detector. At step 501, the ambient environment of the hazard detector may be monitored for hazards. At this time, the hazard detector may be set to a non-alarm state. The hazard detector may monitor for one or multiple types of hazards, including smoke and carbon monoxide. It should be understood that throughout method 500, sensors of the hazard detector may continue to measure levels of hazardous conditions, if any, present in the ambient environment of the hazard detector. For instance, referring to hazard detector 200, carbon monoxide sensor 121 and smoke sensor 122 may provide hazard measurements to processing system 110 for analysis.

At step 505, a hazardous condition may be determined to be present in the environment of a hazard detector. Such a determination may be made based on one or more measured levels of a hazardous condition being compared to a stored threshold value. The hazard may involve the presence of smoke, which can be indicative of fire, carbon monoxide, or some other condition or compound that is potentially dangerous to occupants present in the structure in which the hazard detector is installed. At step 505, the hazard detector may be receiving measurements of the amount of detected hazard in the environment of the hazard detector from one or more sensors of the hazard detector.

At step 510, a state of the hazard detector may be set to be indicative of the hazardous condition being present. Referring back to FIGS. 3A-3C, step 510 may involve the hazard detector being set from a non-alarm state to either a pre-alarm state or an alarm state. An indication of the current state of the hazard detector may be stored by the processing system of the hazard detector, such as to a non-transitory storage medium. While step 510, and later steps of method 500 are being performed, the hazard detector may continue to monitor for hazards in the ambient environment of the hazard detector. At step 510, depending on the state of the hazard detector, the hazard detector may be outputting one or more visual and/or auditory indications. If the hazard detector is in a pre-alarm state, the hazard detector may output a warning that the amount of hazard in the ambient environment of the hazard detector is rising and illuminate a light to be indicative of the pre-alarm state. If the hazard detector is in the alarm mode the hazard detector may sound the alarm and illuminate a light to be indicative of the alarm state.

At step 515, while continuing to monitor the amount of the hazardous condition in the ambient environment of the hazard detector, the hazard detector may determine that the amount of the hazardous condition in the ambient environment is now below a stored, threshold value. This determination may be based on one or more measurements of hazard level made after step 505 was performed. Therefore, the amount of the hazardous condition in the ambient environment of the hazard detector may have decreased since step 505. The first threshold value used at step 505 to determine that the hazardous condition was present in the ambient environment of the hazard detector may be the same stored threshold value used in the determination of step 515. Alternatively, the two threshold values may be different. For example, the threshold value used at step 515 may be smaller in magnitude than the threshold value used to determine that the hazardous condition was present at step 505.

At step 520, in response to the amount of the hazardous condition being determined to be below the stored threshold value, a period of time for which measurements of the hazardous condition have remained below the threshold value may be tracked. If the amount of hazard detected in the ambient environment of the hazard detector exceeds a threshold value (which could be the threshold used at step 515 or 505), the time period may be reset/restarted and/or additional steps may be taken, such as sounding an alarm or making an announcement that the amount of hazard in the environment is rising.

At step 525, a threshold duration may be determined based on one or more factors. The threshold duration may be determined using: the type of hazard detected, the number of hazard detectors that have detected the hazard, the state of the hazard detector, characteristics of the hazard, and/or a measured humidity level in the ambient environment of the hazard detector. The hazard detector may have stored data indicative of how a threshold duration should be determined in view of such factors. Further detail regarding how the threshold duration can be determined is presented in relation to method 600 of FIG. 6. It should be understood that rather than being performed following step 520, step 525 may also be performed at some time prior to step 520.

At step 530, it may be determined that the period of time which was tracked at step 520 has reached at least the threshold duration determined at step 530. The period of time may cease being tracked once step 530 is performed. In response to step 530, step 535 may be performed.

At step 535, the hazard detector may output one or more indications of the hazardous condition easing in response to step 530 being performed. The indications of the hazardous condition easing may include: an auditory message, which may include a synthesized or recorded spoken message, and/or a visual indication, such as a light of the hazard detector illuminating a color that is not typically associated with a hazard, such as green or blue.

At step 540, in response to the period of time having reached at least the threshold duration of step 530 and/or step 535 having been performed, the state of the hazard detector may be downgraded such as in accordance with the embodiments of FIGS. 3A-3C. For example, from an alarm state, the hazard detector may be set to either a non-alarm state or a type of pre-alarm state. If the hazard detector was set to a pre-alarm state at step 510, the hazard detector may be set to a non-alarm state. Method 500 may then return to step 501 to monitor for hazards. If the hazard detector is to be set to a pre-alarm state from an alarm state (or other pre-alarm state), such as flows 313, 316, 317, or 318 of FIGS. 3B and 3C, method 500 may follow the dotted path and perform step 510 in lieu of step 540. At step 510, the state of the hazard detector may be set to the downgraded state of a pre-alarm condition. A different threshold amount may be used for the evaluation of step 515 when performing method 500 again. Further, the threshold duration may be determined to have a different duration based on the current state of the hazard detector.

Figure 6:
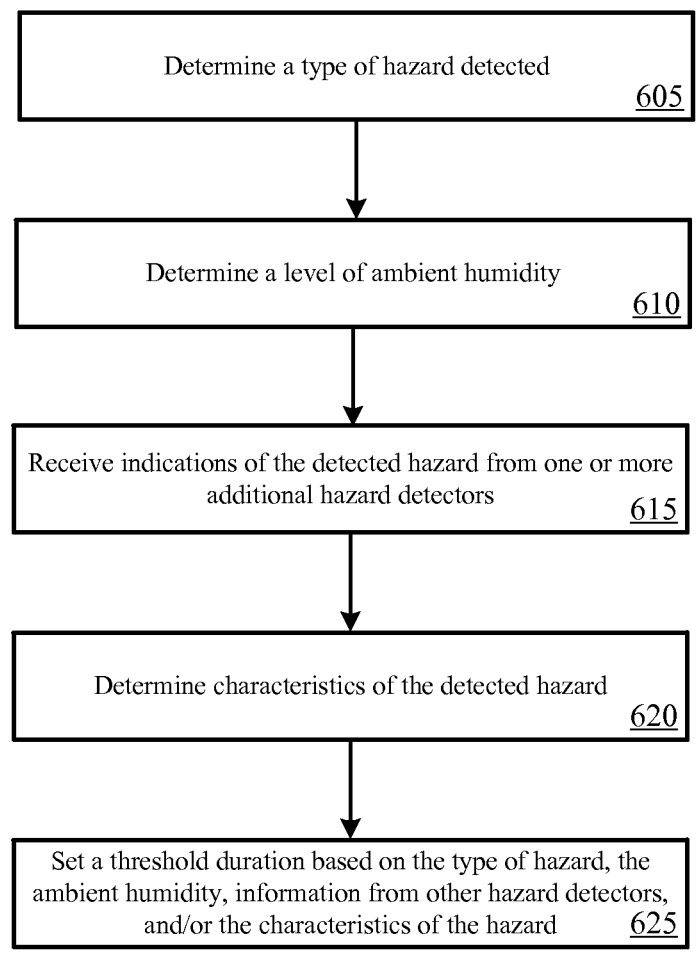
FIG. 6 illustrates an embodiment of a method for determining a threshold duration value to use in assessing whether a hazardous condition has eased.

FIG. 6 illustrates an embodiment of a method 600 for determining a threshold duration value to use in assessing whether a hazardous condition has eased. Method 600 may be performed as part of method 400, method 500, or as part of some other method. For instance, method 600 may be performed as part of step 525 of method 500. Each step of method 600 may generally be performed by a hazard detector. Throughout method 600, one or more sensors of the hazard detector may continue to monitor for and measure amounts of hazardous conditions, such as smoke and/or carbon monoxide, in the ambient environment of the hazard detector. Various factors may be used to determine the duration of the threshold used in determining when the hazard detector should inform user that the hazardous condition is easing. The various determinations performed as part of method 600 may be performed in a varying order. As such, method 600 represents a possible embodiment with various other embodiments being possible.

At step 605, a type of hazard detected may be determined. For each particular type of hazard, a default or minimum threshold duration value may be stored by (or be otherwise accessible to) the hazard detector. For instance, a fire/smoke hazard may be associated with a first duration while a carbon monoxide hazard may be associated with a second, different duration. The type of hazard may be determined based on, for example, the type of hazard that exceeded the threshold of step 505 of method 500. In some embodiments, if multiple hazards are present, a third threshold duration may be selected.

At step 610, an amount of ambient humidity may be determined using one or more humidity sensors of the hazard detector. For instance, humidity sensor 241 of hazard detector 200 may be used to determine the ambient humidity level. The humidity level may be assessed for a current value and/or to determine whether the humidity level is rising or falling. The hazard detector may store a table or other data storage arrangement that relates ranges of humidity levels to an indication of the threshold duration. For instance, the hazard detector may store a table or other data storage arrangement that indicates that if the detected humidity level is between 10%-20%, the threshold duration may be increased by one minute. In some embodiments, an algorithm is stored to calculate how the threshold duration should be set based on the detected humidity level. The threshold duration may also be set or adjusted based on whether the ambient humidity level is rising or falling. While step 610 is focused on humidity, it should be understood that temperature may be additionally or alternatively used in determining the threshold duration. Additionally or alternatively, carbon monoxide levels may be measured. The level of detected carbon monoxide may be used to adjust the threshold duration (and/or a level of sensitivity to smoke).

At step 615, the hazard detector, via a wireless or wired communication module, may receive one or more indications of other hazard detectors located within the same structure as the hazard detector indicative of whether the same (or different) hazard is being detected in those locations. If a hazard is detected in multiple locations within a structure, such as in different rooms, it may be indicative that the hazardous condition is widespread in the structure and may be more likely to be a significant safety concern. The hazard detector may receive signals from other hazard detectors that indicates whether or not a hazard has been detected by such other hazard detectors. In some embodiments, the hazard detector may store indications of the locations and/or numbers of hazard detectors that are installed within the same structure as the hazard detector. If no indication is received from such hazard detectors, it may be assumed that such hazard detectors are not sensing the presence of the hazard. In some embodiments, the hazard detector may poll other hazard detectors to determine levels of the hazardous condition in other locations within the structure. The presence of multiple different types of hazards within the structure may also be determined by the hazard detector by receiving data from other hazard detectors. The threshold duration may be set or adjusted based on in which other locations the hazard was detected, the level of the hazard detected in other locations, and/or at how many hazard detectors the hazard was detected. In some embodiments, an easing message may not be output by the hazard detector until the hazard level remains below the threshold amount for at least the threshold duration at every hazard detector within the structure in which the hazard detector is installed.

At step 620, characteristics of the hazardous condition may be evaluated. These characteristics may be used to set or adjust the threshold duration. For instance, characteristics of the hazardous condition may involve a determination of the rapidity with which the amount of the hazard increased in the ambient environment of the hazard detector (e.g., slow, smoldering fire or fast, smoky fire), the maximum amount of the hazardous condition detected, the mean/media amount of the hazardous condition detected, other hazardous conditions detected during the same time period, the amount of time for which the hazardous condition has been detected, etc. In some embodiments, the hazardous condition may be compared to stored profiles of various types of hazardous conditions, such as grease fires, electrical fires, furnace carbon monoxide leakage, etc., to classify the hazardous condition. The profile selected and/or the characteristics analyzed may be used to set or adjust the threshold duration.

At step 625, at least some of the factors determined in relation to steps 605-through 620, and possibly additional factors, may be used in determining the threshold duration. In some embodiments, a default threshold duration is used as a starting point and is then adjusted based on the factors at step 625. For instance, the presence of a factor (e.g., two other hazard detectors having detected the hazard) may involve the threshold duration being increased by a predefined amount of time, such as three minutes. Such adjustments that can be implemented based on such factors may be stored by the hazard detector, such as in the form of a look-up table. In some embodiments, an algorithm may take each of the determined factors into account to calculate a threshold duration. The longer the duration, the longer the amount of time that must elapse with the amount of hazard remaining below the threshold value before the hazard detector outputs an indication that the amount of the hazard in the environment of the hazard detector is easing.

Figure 7:
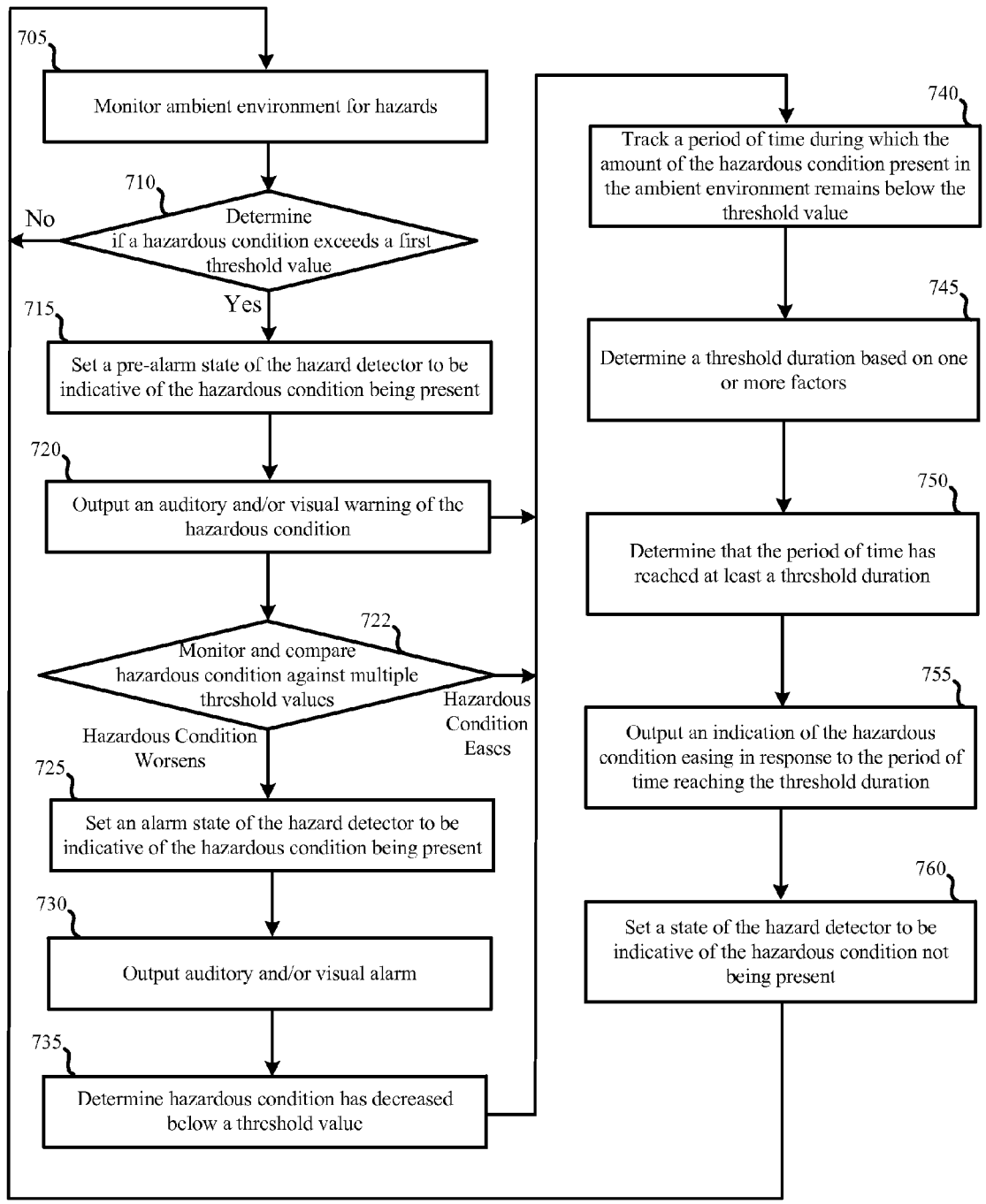
FIG. 7 illustrates an embodiment of a method for using a pre-alarm state of a hazard detector to alert a user to the presence and easing of a hazardous condition.

FIG. 7 illustrates an embodiment of a method 700 for using a pre-alarm state of a hazard detector to alert a user to the presence and easing of a hazardous condition. Method 700 may be performed using hazard detector 100, hazard detector 200, or some other embodiment of a hazard detector. Method 500 may represent a more detailed embodiment of method 400 and/or method 500. Each step of method 700 may generally be performed by a hazard detector. Throughout method 700, one or more sensors of the hazard detector may continue to monitor for and measure amounts of hazardous conditions, such as smoke and/or carbon monoxide, in the ambient environment of the hazard detector.

At step 705, the ambient environment of the hazard detector may be monitored for hazards. At this step, the hazard detector may be set to a non-alarm state. The hazard detector may monitor for multiple types of hazards, including smoke and carbon monoxide. It should be understood that throughout method 700, one or more sensors of the hazard detector may continue to monitor for levels of hazards, if any, present in the ambient environment of the hazard detector. For instance, referring to hazard detector 200, carbon monoxide sensor 121 and smoke sensor 122 may provide hazard measurements to processing system 110 for analysis.

At step 710, it may be determined if a hazardous condition is present in the environment of a hazard detector. Such a determination may be made based on one or more measured levels of a hazardous condition being compared to a stored threshold value. The hazard may involve the presence of smoke, which can be indicative of fire, carbon monoxide, or some other condition or compound that is potentially dangerous to occupants present in the structure in which the hazard detector is installed. Referring to hazard detector 200 of FIG. 2 for example, hazard monitor engine 112 may determine that a hazard is present by comparing a measured value from either carbon monoxide sensor 121 or smoke sensor 122 to a corresponding threshold value from hazard thresholds 114. If the measured hazardous condition meets and/or exceeds a first threshold value, method 700 may proceed to step 715; otherwise the hazard detector continues to monitor for hazardous conditions at step 705.

At step 715, a state of the hazard detector may be set to be indicative of the hazardous condition being present. Referring back to FIGS. 3A-3C, step 715 may involve the hazard detector being set from a non-alarm state to a pre-alarm state. An indication of the current state of the hazard detector may be stored by the processing system of the hazard detector, such as to a non-transitory storage medium. While step 715 is being performed, and later steps of method 500 are being performed, the hazard detector may continue to monitor for hazards in the ambient environment of the hazard detector. Referring to hazard detector 200 of FIG. 2 for example, state engine 111 may have its state set to a pre-alarm state (e.g., a first pre-alarm state, a second pre-alarm state).

At step 720, the hazard detector may be outputting one or more visual and/or auditory indications. The hazard detector has been set to a pre-alarm state based on the detected hazard level of step 710, the hazard detector may output an auditory warning, which may include a message containing speech, stating that the amount of hazard in the ambient environment of the hazard detector is rising and illuminate a light to be indicative of the pre-alarm state. For example, such a light may be illuminated using a color typically associated with a problem or hazard, such as yellow or red.

The hazard detector may continue to monitor the hazard level in the ambient environment of the hazard detector at step 722. The hazard detector may monitor the level of detected hazard to determine if it exceeds a second threshold value (which is representative of a greater amount of the hazard being present than the first threshold value used at step 710) or if the amount of hazard falls below a third threshold value, which may match the first threshold value or may be a smaller in magnitude than the first threshold value. If the amount of hazard remains between the second and third threshold value, method 700 may remain at step 722 until one of the threshold values is met. Referring to FIG. 3B, the hazard detector may be in pre-alarm state 303. If the second threshold is exceeded, the state of the hazard detector will transition to alarm state 302. If the third threshold is met, the state of the hazard detector may transition to non-alarm state 301 (following one or more other conditions being met).

If the hazardous condition worsens at step 722 and the level of hazard detected by the hazard detector exceeds the second threshold value, method 700 may proceed to step 725. At step 725, a state of the hazard detector may be set to an alarm state. An indication of the alarm state of the hazard detector may be stored by the processing system of the hazard detector, such as to a non-transitory storage medium. At step 730 and auditory and/or a visual alarm may be output to alert the user to the alarm state. The hazard detector may output an alarm sound and/or an auditory message, which may include speech, stating that the amount of hazard in the ambient environment of the hazard detector is dangerous and illuminate a light to be indicative of the alarm state. For example, such a light may be illuminated a color typically associated with a problem or hazard, such as yellow or red. An animation indicative of the severity of the hazard may also be output, such as by flashing the light rapidly.

At step 735, after the auditory and/or visual alarm has been sounding for a period of time, the hazard detector may determine that the hazardous condition has decreased below the third threshold value. In response to the hazardous level decreased below the third threshold value, method 700 may proceed to step 740. Returning to step 722, if is determined that the hazardous condition meets or falls below the third threshold value, method 700 may proceed to step 740 without performing steps 725 through 735. As such, at the start of step 740, the hazard detector may be set to either a pre-alarm state or an alarm state.

At step 740, in response to the amount of the hazardous condition being determined to be below the third threshold value, a period of time for which measurements of the hazardous condition have remained below the threshold value may be tracked. For instance, a counter of the hazard detector may be initiated or a timestamp may be created. If the amount of hazard detected in the ambient environment of the hazard detector exceeds the third threshold value again, the time period may be reset and/or additional steps may be taken, such as sounding an alarm or making an announcement that the amount of hazard in the environment is rising or returning to step 722 or step 715.

At step 745, a threshold duration may be determined based on one or more factors. The threshold duration may be determined using: the type of hazard detected, the number of hazard detectors that have detected the hazard, the state of the hazard detector, characteristics of the hazard, and/or a measured humidity level in the ambient environment of the hazard detector. The hazard detector may have stored data indicative of how a threshold duration should be determined in view of such factors. Further detail regarding how the threshold duration can be determined is presented in relation to method 600 of FIG. 6. It should be understood that rather than being performed following step 740, step 745 may also be performed at some time prior to step 740.

At step 750, it may be determined that the period of time which was started to be tracked at step 740 has reached at least the threshold duration determined at step 745. The period of time may cease being tracked once step 750 is performed (e.g., a counter may be disabled). In response to step 750, step 755 may be performed.

At step 755, the hazard detector may output one or more indications of the hazardous condition easing in response to step 750 being performed. The indications of the hazardous condition easing may include: an auditory message, which may include a synthesized or recorded spoken message, and/or a visual indication, such as a light of the hazard detector illuminating a color that is not typically associated with a hazard, such as green or blue. If a spoken message is output, the message may indicate in which room the hazard detector is located. For instance, the message may be: "[Hazard] is clearing in the [room]." Where [hazard] is the type of hazard (smoke, carbon monoxide, etc.) and [room] is the room that was designated as the location in which the hazard detector was installed by a user during a set up process. In some embodiments, the hazard detector may communicate that the hazardous condition is easing to the other hazard detectors located within the same structure as in which the hazard detector is installed. Step 755 may further include a chime or other sound being output to signal that the hazard is clear. In some embodiment a light pattern, such as a pulse of green light is output by the hazard detector to be indicative of the hazard clearing. The auditory and/or visual message may then be output through such other hazard detectors installed within the structure.

At step 760, the state of the hazard detector may be downgraded such as in accordance with the embodiments of FIGS. 3A-3C such as to a non-alarm state. Method 700 may then return to step 705 to monitor for hazards in the non-alarm state. In the non-alarm state, the hazard detector may not be outputting any visual and/or auditory warnings regarding hazardous conditions.

Method 700 is focused on a single pre-alarm state being used, however, it should be understood that method 700 may be applied to embodiments that have multiple pre-alarm states, such as state flow 300C of FIG. 3C. For instance, between steps 720 and 722, an additional iteration of steps 722 through 730 may be added to evaluate a second pre-alarm state and output a warning corresponding to the second pre-alarm state (e.g., more urgent than a first pre-alarm state but less urgent than an alarm state). Such a second pre-alarm state may use a fourth threshold value, different than the first threshold value, to evaluate if the hazard detector has entered into the second pre-alarm state. The second and third thresholds may still be used to determine if the hazard detector should enter an alarm state (the hazardous condition worsens) or indicate that the hazardous condition is easing and return to either a lower pre-alarm state or the non-alarm state.

Figure 8:
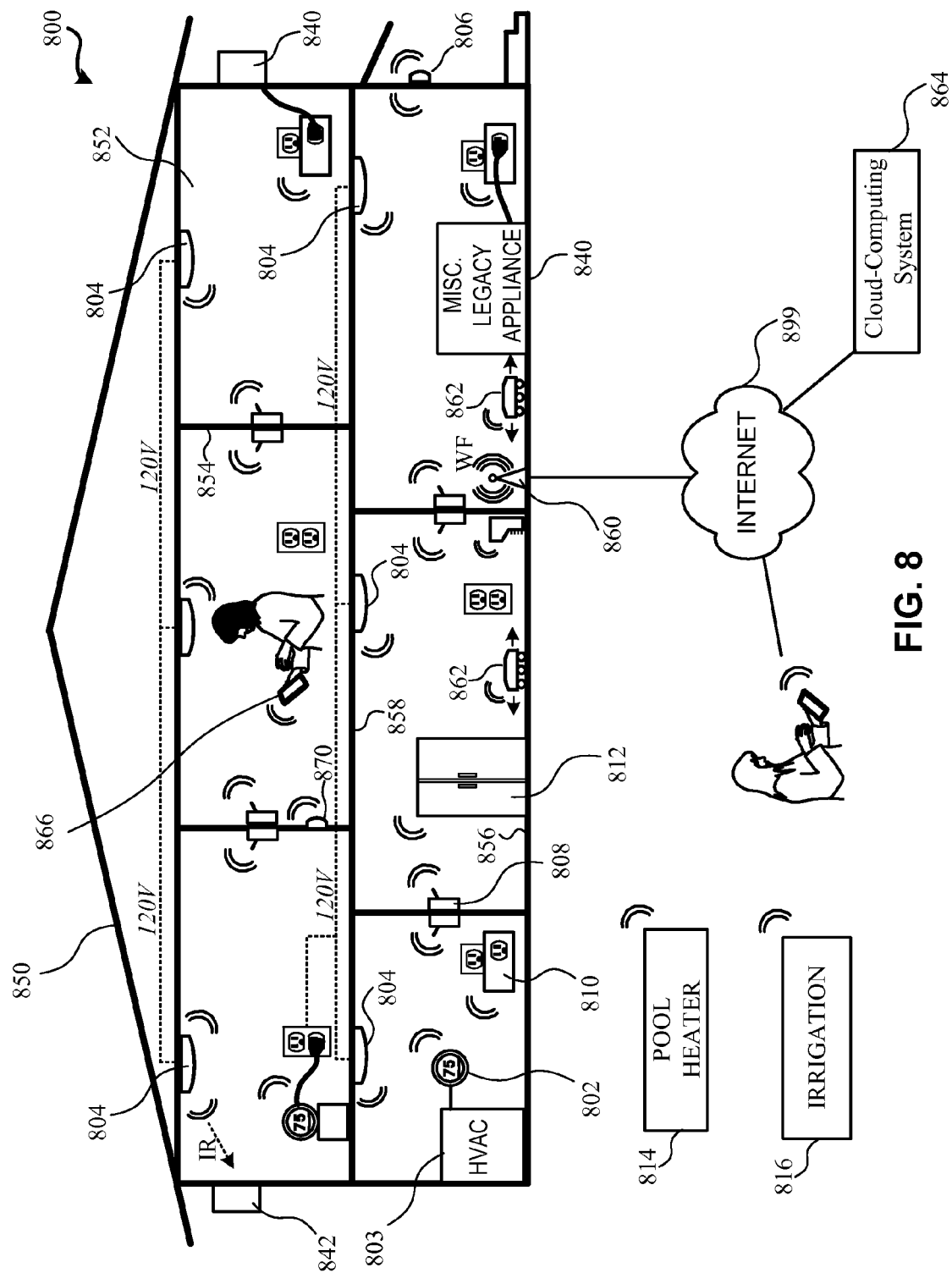
FIG. 8 illustrates an example of a smart-home environment within which one or more hazard devices can be installed.

Hazard detectors, as detailed herein, may be installed in a smart-home environment. FIG. 8 illustrates an example of a smart-home environment 800 within which one or more of the devices, methods, systems, services, and/or computer program products described further herein can be applicable. The depicted smart-home environment 800 includes a structure 850, which can include, e.g., a house, office building, garage, or mobile home. It will be appreciated that devices can also be integrated into a smart-home environment 800 that does not include an entire structure 850, such as an apartment, condominium, or office space. Further, the smart home environment can control and/or be coupled to devices outside of the actual structure 850. Indeed, several devices in the smart home environment need not physically be within the structure 850 at all. For example, a device controlling a pool heater or irrigation system can be located outside of the structure 850.

The depicted structure 850 includes a plurality of rooms 852, separated at least partly from each other via walls 854. The walls 854 can include interior walls or exterior walls. Each room can further include a floor 856 and a ceiling 858. Devices can be mounted on, integrated with and/or supported by a wall 854, floor 856 or ceiling 858.

In some embodiments, the smart-home environment 800 of FIG. 8 includes a plurality of devices, including intelligent, multi-sensing, network-connected devices, that can integrate seamlessly with each other and/or with a central server or a cloud-computing system to provide any of a variety of useful smart-home objectives. The smart-home environment 800 may include one or more intelligent, multi-sensing, network-connected thermostats 802 (hereinafter referred to as smart thermostats 802), one or more intelligent, network-connected, hazard detectors 804, and one or more intelligent, multi-sensing, network-connected entryway interface devices 806 (hereinafter referred to as "smart doorbells 806"). According to embodiments, the smart thermostat 802 detects ambient climate characteristics (e.g., temperature and/or humidity) and controls a HVAC system 803 accordingly. The hazard detector 804 may detect the presence of a hazardous substance or a substance indicative of a hazardous substance (e.g., smoke, fire, or carbon monoxide). The smart doorbell 806 may detect a person's approach to or departure from a location (e.g., an outer door), control doorbell functionality, announce a person's approach or departure via audio or visual means, or control settings on a security system (e.g., to activate or deactivate the security system when occupants go and come).

In some embodiments, the smart-home environment 800 of FIG. 8 further includes one or more intelligent, multi-sensing, network-connected wall switches 808 (hereinafter referred to as "smart wall switches 808"), along with one or more intelligent, multi-sensing, network-connected wall plug interfaces 810 (hereinafter referred to as "smart wall plugs 810"). The smart wall switches 808 may detect ambient lighting conditions, detect room-occupancy states, and control a power and/or dim state of one or more lights. In some instances, smart wall switches 808 may also control a power state or speed of a fan, such as a ceiling fan. The smart wall plugs 810 may detect occupancy of a room or enclosure and control supply of power to one or more wall plugs (e.g., such that power is not supplied to the plug if nobody is at home).

Still further, in some embodiments, the smart-home environment 800 of FIG. 8 includes a plurality of intelligent, multi-sensing, network-connected appliances 812 (hereinafter referred to as "smart appliances 812"), such as refrigerators, stoves and/or ovens, televisions, washers, dryers, lights, stereos, intercom systems, garage-door openers, floor fans, ceiling fans, wall air conditioners, pool heaters, irrigation systems, security systems, and so forth. According to embodiments, the network-connected appliances 812 are made compatible with the smart-home environment by cooperating with the respective manufacturers of the appliances. For example, the appliances can be space heaters, window AC units, motorized duct vents, etc. When plugged in, an appliance can announce itself to the smart-home network, such as by indicating what type of appliance it is, and it can automatically integrate with the controls of the smart-home. Such communication by the appliance to the smart home can be facilitated by any wired or wireless communication protocols known by those having ordinary skill in the art. The smart home also can include a variety of non-communicating legacy appliances 840, such as old conventional washer/dryers, refrigerators, and the like which can be controlled, albeit coarsely (ON/OFF), by virtue of the smart wall plugs 810. The smart-home environment 800 can further include a variety of partially communicating legacy appliances 842, such as infrared ("IR") controlled wall air conditioners or other IR-controlled devices, which can be controlled by IR signals provided by the hazard detectors 804 or the smart wall switches 808.

According to embodiments, the smart thermostats 802, the hazard detectors 804, the smart doorbells 806, the smart wall switches 808, the smart wall plugs 810, and other devices of the smart-home environment 800 are modular and can be incorporated into older and new houses. For example, the devices are designed around a modular platform consisting of two basic components: a head unit and a back plate, which is also referred to as a docking station. Multiple configurations of the docking station are provided so as to be compatible with any home, such as older and newer homes. However, all of the docking stations include a standard head-connection arrangement, such that any head unit can be removably attached to any docking station. Thus, in some embodiments, the docking stations are interfaces that serve as physical connections to the structure and the voltage wiring of the homes, and the interchangeable head units contain all of the sensors, processors, user interfaces, the batteries, and other functional components of the devices.

The smart-home environment 800 may also include communication with devices outside of the physical home, but within a proximate geographical range of the home. For example, the smart-home environment 800 may include a pool heater monitor 814 that communicates a current pool temperature to other devices within the smart-home environment 800 or receives commands for controlling the pool temperature. Similarly, the smart-home environment 800 may include an irrigation monitor 816 that communicates information regarding irrigation systems within the smart-home environment 800 and/or receives control information for controlling such irrigation systems. According to embodiments, an algorithm is provided for considering the geographic location of the smart-home environment 800, such as based on the zip code or geographic coordinates of the home. The geographic information is then used to obtain data helpful for determining optimal times for watering; such data may include sun location information, temperature, due point, soil type of the land on which the home is located, etc.

By virtue of network connectivity, one or more of the smart-home devices of FIG. 8 can further allow a user to interact with the device even if the user is not proximate to the device. For example, a user can communicate with a device using a computer (e.g., a desktop computer, laptop computer, or tablet) or other portable electronic device (e.g., a smartphone) 866. A webpage or app can be configured to receive communications from the user and control the device based on the communications and/or to present information about the device's operation to the user. For example, the user can view a current setpoint temperature for a device and adjust it, using a computer. The user can be in the structure during this remote communication or outside the structure.

As discussed, users can control and interact with the smart thermostat, hazard detectors 804, and other smart devices in the smart-home environment 800 using a network-connected computer or portable electronic device 866. In some examples, some or all of the occupants (e.g., individuals who live in the home) can register their device 866 with the smart-home environment 800. Such registration can be made at a central server to authenticate the occupant and/or the device as being associated with the home and to give permission to the occupant to use the device to control the smart devices in the home. An occupant can use his registered device 866 to remotely control the smart devices of the home, such as when the occupant is at work or on vacation. The occupant may also use his registered device to control the smart devices when the occupant is actually located inside the home, such as when the occupant is sitting on a couch inside the home. It should be appreciated that, instead of or in addition to registering devices 866, the smart-home environment 800 makes inferences about which individuals live in the home and are therefore occupants and which devices 866 are associated with those individuals. As such, the smart-home environment "learns" who is an occupant and permits the devices 866 associated with those individuals to control the smart devices of the home.

In some embodiments, in addition to containing processing and sensing capabilities, each of the devices 802, 804, 806, 808, 810, 812, 814, and 816 (collectively referred to as "the smart devices") is capable of data communications and information sharing with any other of the smart devices, as well as to any central server or cloud-computing system or any other device that is network-connected anywhere in the world. The required data communications can be carried out using any of a variety of custom or standard wireless protocols (Wi-Fi, ZigBee, 6LoWPAN, etc.) and/or any of a variety of custom or standard wired protocols (CAT6 Ethernet, HomePlug, etc.).

According to embodiments, all or some of the smart devices can serve as wireless or wired repeaters. For example, a first one of the smart devices can communicate with a second one of the smart devices via a wireless router 860. The smart devices can further communicate with each other via a connection to a network, such as the Internet 899. Through the Internet 899, the smart devices can communicate with a cloud-computing system 864, which can include one or more centralized or distributed server systems. The cloud-computing system 864 can be associated with a manufacturer, support entity, or service provider associated with the device. For one embodiment, a user may be able to contact customer support using a device itself rather than needing to use other communication means such as a telephone or Internet-connected computer. Further, software updates can be automatically sent from cloud-computing system 864 to devices (e.g., when available, when purchased, or at routine intervals).

According to embodiments, the smart devices combine to create a mesh network of spokesman and low-power nodes in the smart-home environment 800, where some of the smart devices are "spokesman" nodes and others are "low-powered" nodes. Some of the smart devices in the smart-home environment 800 are battery powered, while others have a regular and reliable power source, such as by connecting to wiring (e.g., to 120V line voltage wires) behind the walls 854 of the smart-home environment. The smart devices that have a regular and reliable power source are referred to as "spokesman" nodes. These nodes are equipped with the capability of using any wireless protocol or manner to facilitate bidirectional communication with any of a variety of other devices in the smart-home environment 800 as well as with the cloud-computing system 864. On the other hand, the devices that are battery powered are referred to as "low-power" nodes. These nodes tend to be smaller than spokesman nodes and can only communicate using wireless protocols that require very little power, such as Zigbee, 6LoWPAN, etc. Further, some, but not all, low-power nodes are incapable of bidirectional communication. These low-power nodes send messages, but they are unable to "listen". Thus, other devices in the smart-home environment 800, such as the spokesman nodes, cannot send information to these low-power nodes.

As described, the smart devices serve as low-power and spokesman nodes to create a mesh network in the smart-home environment 800. Individual low-power nodes in the smart-home environment regularly send out messages regarding what they are sensing, and the other low-powered nodes in the smart-home environment—in addition to sending out their own messages—repeat the messages, thereby causing the messages to travel from node to node (i.e., device to device) throughout the smart-home environment 800. The spokesman nodes in the smart-home environment 800 are able to "drop down" to low-powered communication protocols to receive these messages, translate the messages to other communication protocols, and send the translated messages to other spokesman nodes and/or cloud-computing system 864. Thus, the low-powered nodes using low-power communication protocols are able to send messages across the entire smart-home environment 800 as well as over the Internet 899 to cloud-computing system 864. According to embodiments, the mesh network enables cloud-computing system 864 to regularly receive data from all of the smart devices in the home, make inferences based on the data, and send commands back to one of the smart devices to accomplish some of the smart-home objectives described herein.

As described, the spokesman nodes and some of the low-powered nodes are capable of "listening." Accordingly, users, other devices, and cloud-computing system 864 can communicate controls to the low-powered nodes. For example, a user can use the portable electronic device (e.g., a smartphone) 866 to send commands over the Internet 899 to cloud-computing system 864, which then relays the commands to the spokesman nodes in the smart-home environment 800. The spokesman nodes drop down to a low-power protocol to communicate the commands to the low-power nodes throughout the smart-home environment, as well as to other spokesman nodes that did not receive the commands directly from the cloud-computing system 864.

An example of a low-power node is a smart nightlight 870. In addition to housing a light source, the smart nightlight 870 houses an occupancy sensor, such as an ultrasonic or passive IR sensor, and an ambient light sensor, such as a photodiode, photoresistor, phototransistor, or a single-pixel sensor that measures light in the room. In some embodiments, the smart nightlight 870 is configured to activate the light source when its ambient light sensor detects that the room is dark and when its occupancy sensor detects that someone is in the room. In other embodiments, the smart nightlight 870 is simply configured to activate the light source when its ambient light sensor detects that the room is dark. Further, according to embodiments, the smart nightlight 870 includes a low-power wireless communication chip (e.g., ZigBee chip) that regularly sends out messages regarding the occupancy of the room and the amount of light in the room, including instantaneous messages coincident with the occupancy sensor detecting the presence of a person in the room. As mentioned above, these messages may be sent wirelessly, using the mesh network, from node to node (i.e., smart device to smart device) within the smart-home environment 800 as well as over the Internet 899 to cloud-computing system 864.

Other examples of low-powered nodes include battery-operated versions of the hazard detectors 804. These hazard detectors 804 are often located in an area without access to constant and reliable (e.g., structural) power and, as discussed in detail below, may include any number and type of sensors, such as smoke/fire/heat sensors, carbon monoxide/dioxide sensors, occupancy/motion sensors, ambient light sensors, flame detectors, air quality sensors (e.g., for VOCs, particulate matter (e.g., PM 2.5), allergens, and other unhealthy contaminants such as NOx), temperature sensors, humidity sensors, and the like. Furthermore, hazard detectors 804 can send messages that correspond to each of the respective sensors to the other devices and cloud-computing system 864, such as by using the mesh network as described above.

Examples of spokesman nodes include smart doorbells 806, smart thermostats 802, smart wall switches 808, and smart wall plugs 810. These devices 802, 806, 808, and 810 are often located near and connected to a reliable power source, and therefore can include more power-consuming components, such as one or more communication chips capable of bidirectional communication in any variety of protocols.

In some embodiments, the mesh network of low-powered and spokesman nodes can be used to provide exit lighting in the event of an emergency. In some instances, to facilitate this, users provide pre-configuration information that indicates exit routes in the smart-home environment 800. For example, for each room in the house, the user provides a map of the best exit route. It should be appreciated that instead of a user providing this information, cloud-computing system 864 or some other device could automatically determine the routes using uploaded maps, diagrams, architectural drawings of the smart-home house, as well as using a map generated based on positional information obtained from the nodes of the mesh network (e.g., positional information from the devices is used to construct a map of the house). In operation, when an alarm is activated (e.g., when one or more of the hazard detector 804 detects smoke and activates an alarm), cloud-computing system 864 or some other device uses occupancy information obtained from the low-powered and spokesman nodes to determine which rooms are occupied and then turns on lights (e.g., smart nightlights 870, wall switches 808, smart wall plugs 810 that power lamps, etc.) along the exit routes from the occupied rooms so as to provide emergency exit lighting.

Further included and illustrated in the exemplary smart-home environment 800 of FIG. 8 are service robots 862 each configured to carry out, in an autonomous manner, any of a variety of household tasks. For some embodiments, the service robots 862 can be respectively configured to perform floor sweeping, floor washing, etc. in a manner similar to that of known commercially available devices such as the Roomba™ and Scooba™ products sold by iRobot, Inc. of Bedford, Mass. Tasks such as floor sweeping and floor washing can be considered as "away" or "while-away" tasks for purposes of the instant description, as it is generally more desirable for these tasks to be performed when the occupants are not present. For other embodiments, one or more of the service robots 862 are configured to perform tasks such as playing music for an occupant, serving as a localized thermostat for an occupant, serving as a localized air monitor/purifier for an occupant, serving as a localized baby monitor, serving as a localized hazard detector for an occupant, and so forth, it being generally more desirable for such tasks to be carried out in the immediate presence of the human occupant. For purposes of the instant description, such tasks can be considered as "human-facing" or "human-centric" tasks.

When serving as a localized air monitor/purifier for an occupant, a particular service robot 862 can be considered to be facilitating what can be called a "personal health-area network" for the occupant, with the objective being to keep the air quality in the occupant's immediate space at healthy levels. Alternatively or in conjunction therewith, other health-related functions can be provided, such as monitoring the temperature or heart rate of the occupant (e.g., using finely remote sensors, near-field communication with on-person monitors, etc.). When serving as a localized hazard detector for an occupant, a particular service robot 862 can be considered to be facilitating what can be called a "personal safety-area network" for the occupant, with the objective being to ensure there is no excessive carbon monoxide, smoke, fire, etc., in the immediate space of the occupant. Methods analogous to those described above for personal comfort-area networks in terms of occupant identifying and tracking are likewise applicable for personal health-area network and personal safety-area network embodiments.

According to some embodiments, the above-referenced facilitation of personal comfort-area networks, personal health-area networks, personal safety-area networks, and/or other such human-facing functionalities of the service robots 862, are further enhanced by logical integration with other smart sensors in the home according to rules-based inferencing techniques or artificial intelligence techniques for achieving better performance of those human-facing functionalities and/or for achieving those goals in energy-conserving or other resource-conserving ways. Thus, for one embodiment relating to personal health-area networks, the air monitor/purifier service robot 862 can be configured to detect whether a household pet is moving toward the currently settled location of the occupant (e.g., using on-board sensors and/or by data communications with other smart-home sensors along with rules-based inferencing/artificial intelligence techniques), and if so, the air purifying rate is immediately increased in preparation for the arrival of more airborne pet dander. For another embodiment relating to personal safety-area networks, the hazard detector service robot 862 can be advised by other smart-home sensors that the temperature and humidity levels are rising in the kitchen, which is nearby the occupant's current dining room location, and responsive to this advisory, the hazard detector service robot 862 will temporarily raise a hazard detection threshold, such as a smoke detection threshold, under an inference that any small increases in ambient smoke levels will most likely be due to cooking activity and not due to a genuinely hazardous condition.

Figure 9:
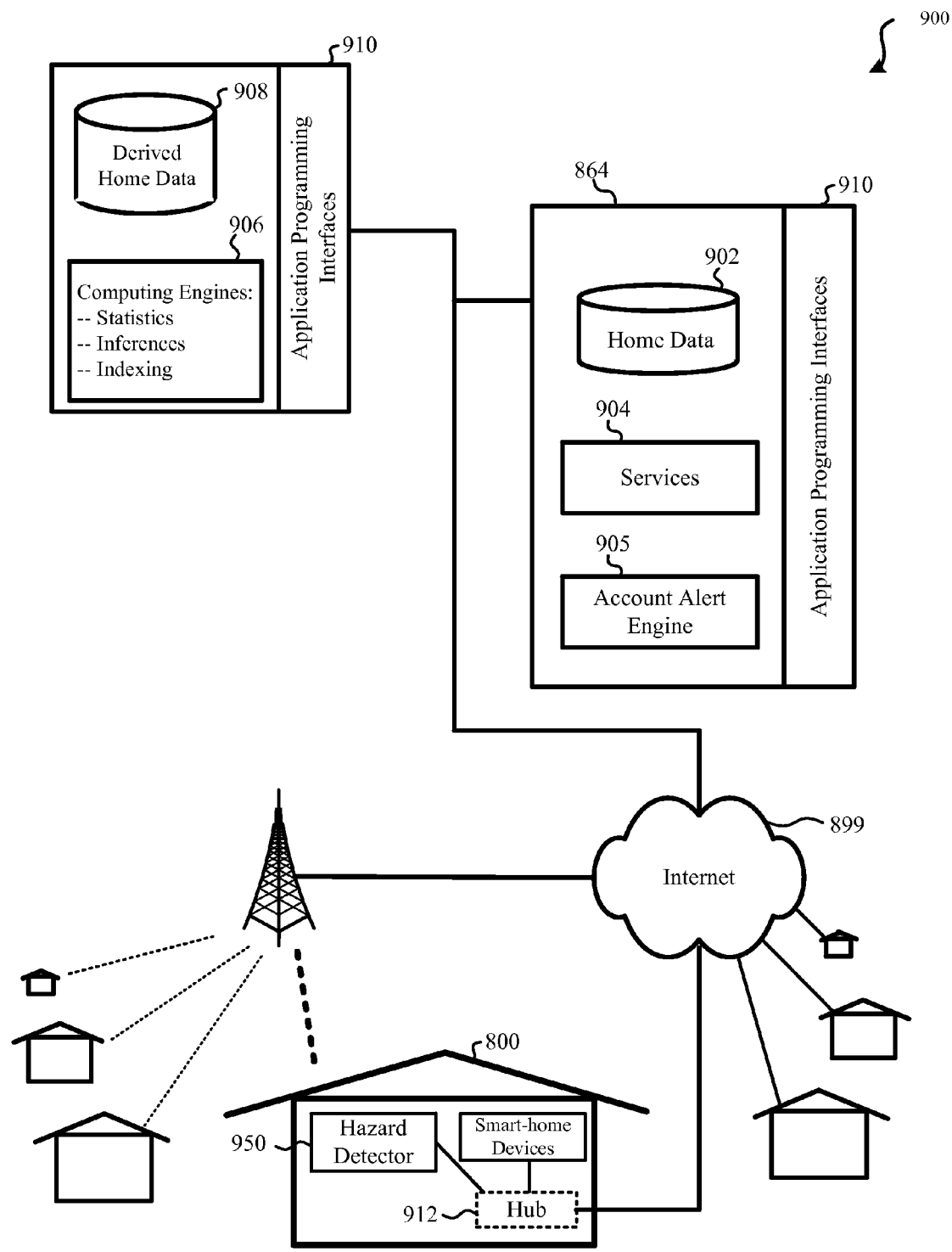
FIG. 9 illustrates a network-level view of the extensible devices and services platform with which a hazard detector may be integrated.

FIG. 9 illustrates a network-level view of an extensible devices and services platform 900 with which a plurality of smart-home environments, such as the smart-home environment 800 of FIG. 8, can be integrated. The extensible devices and services platform 900 includes cloud-computing system 864. Each of the intelligent, network-connected devices 802, 804, 806, 808, 810, 812, 814, and 816 from FIG. 8 may communicate with cloud-computing system 864. For example, a connection to the Internet 899 can be established either directly (for example, using 3G/4G connectivity to a wireless carrier), through a hubbed network 912 (which can be a scheme ranging from a simple wireless router, for example, up to and including an intelligent, dedicated whole-home control node), or through any combination thereof.

Although in some examples provided herein, the devices and services platform 900 communicates with and collects data from the smart devices of smart-home environment 800 of FIG. 8, it should be appreciated that the devices and services platform 900 communicates with and collects data from a plurality of smart-home environments across the world. For example, cloud-computing system 864 can collect home data 902 from the devices of one or more smart-home environments, where the devices can routinely transmit home data or can transmit home data in specific instances (e.g., when a device queries the home data 902). Thus, the devices and services platform 900 routinely collects data from homes across the world. As described, the collected home data 902 includes, for example, power consumption data, occupancy data, HVAC settings and usage data, carbon monoxide levels data, carbon dioxide levels data, volatile organic compounds levels data, sleeping schedule data, cooking schedule data, inside and outside temperature humidity data, television viewership data, inside and outside noise level data, etc.

Cloud-computing system 864 can further provide one or more services 904. The services 904 can include, e.g., software updates, customer support, sensor data collection/logging, remote access, remote or distributed control, or use suggestions (e.g., based on collected home data 902 to improve performance, reduce utility cost, etc.). Data associated with the services 904 can be stored at cloud-computing system 864 and cloud-computing system 864 can retrieve and transmit the data at an appropriate time (e.g., at regular intervals, upon receiving a request from a user, etc.).

As part of services 904, user accounts may be maintained by the cloud-computing system 864. The user account may store subscription information, billing information, registration information, user preferences, and/or other data associated with various smart-home devices, such as one or more hazard detectors, installed within a structure that is linked with a user account. Occasionally, attention of a user to his or her user account may be requested. In response to a query from hazard detector 950 (or other smart-home device), a message may be transmitted by the cloud-computing system 864 to hazard detector 950 (which may represent any of the previously described hazard detectors) indicating that a status output by hazard detector 950 should indicate that a user is requested to log in to his or her user account. Further detail regarding the requested log may be transmitted by service 904 to hazard detector 950. For instance, the reason for the requested login may be expired payment information (such as an expired credit card). The user can request detail on a status output by hazard detector 950, which may be presented to the user as a color and animation output via a light of hazard detector 950. The request for detail may be by performing a gesture within the vicinity of hazard detector 950. A spoken message may then be output by hazard detector 950 indicating that the user is requested to log in to his account and may also indicate the reason of the payment information needing to be updated. As such, a status check performed by hazard detector 950 may not only check the status of hazard detector 950 itself, but also the state of a remotely-maintained user account.

As illustrated in FIG. 9, an embodiment of the extensible devices and services platform 900 includes a processing engine 906, which can be concentrated at a single server or distributed among several different computing entities without limitation. The processing engine 906 can include computerized engines (e.g., software executed by hardware) configured to receive data from devices of smart-home environments (e.g., via the Internet or a hubbed network), to index the data, to analyze the data and/or to generate statistics based on the analysis or as part of the analysis. The analyzed data can be stored as derived home data 908.

Results of the analysis or statistics can thereafter be transmitted back to the device that provided home data used to derive the results, to other devices, to a server providing a webpage to a user of the device, or to other non-device entities. For example, use statistics, use statistics relative to use of other devices, use patterns, and/or statistics summarizing sensor readings can be generated by the processing engine 906 and transmitted. The results or statistics can be provided via the Internet 899. In this manner, the processing engine 906 can be configured and programmed to derive a variety of useful information from the home data 902. A single server can include one or more engines.

In some embodiments, to encourage innovation and research and to increase products and services available to users, the devices and services platform 900 exposes a range of application programming interfaces (APIs) 910 to third parties, such as charities, governmental entities (e.g., the Food and Drug Administration or the Environmental Protection Agency), academic institutions (e.g., university researchers), businesses (e.g., providing device warranties or service to related equipment, targeting advertisements based on home data), utility companies, and other third parties. The APIs 910 may be coupled to and permit third-party systems to communicate with cloud-computing system 864, including the services 904, the processing engine 906, the home data 902, and the derived home data 908. For example, the APIs 910 allow applications executed by the third parties to initiate specific data processing tasks that are executed by cloud-computing system 864, as well as to receive dynamic updates to the home data 902 and the derived home data 908.

Account alert engine may serve to determine whether a hazard detector should provide an indication that the user's account requires attention. For instance, account alert engine 905 may periodically assess the state of a user's account, such as whether settings need updating, whether payment information is up-to-date, whether one or more messages are pending, whether payment is due, etc. If user attention is required, upon a request being received from a hazard detector and a look-up of the user's account being performed, account alert engine may respond with an indication that the user account requires attention. Additional detail may also be provided such that if the user performs a gesture or otherwise requests additional detail, such detail can be provided, such as via an auditory message. If user attention is not required, upon a request being received from a hazard detector and a look-up of the user's account being performed (e.g., by determining an account associated with the hazard detector from which the request was received), account alert engine may respond with an indication that the user account does not require attention.

Figure 10:
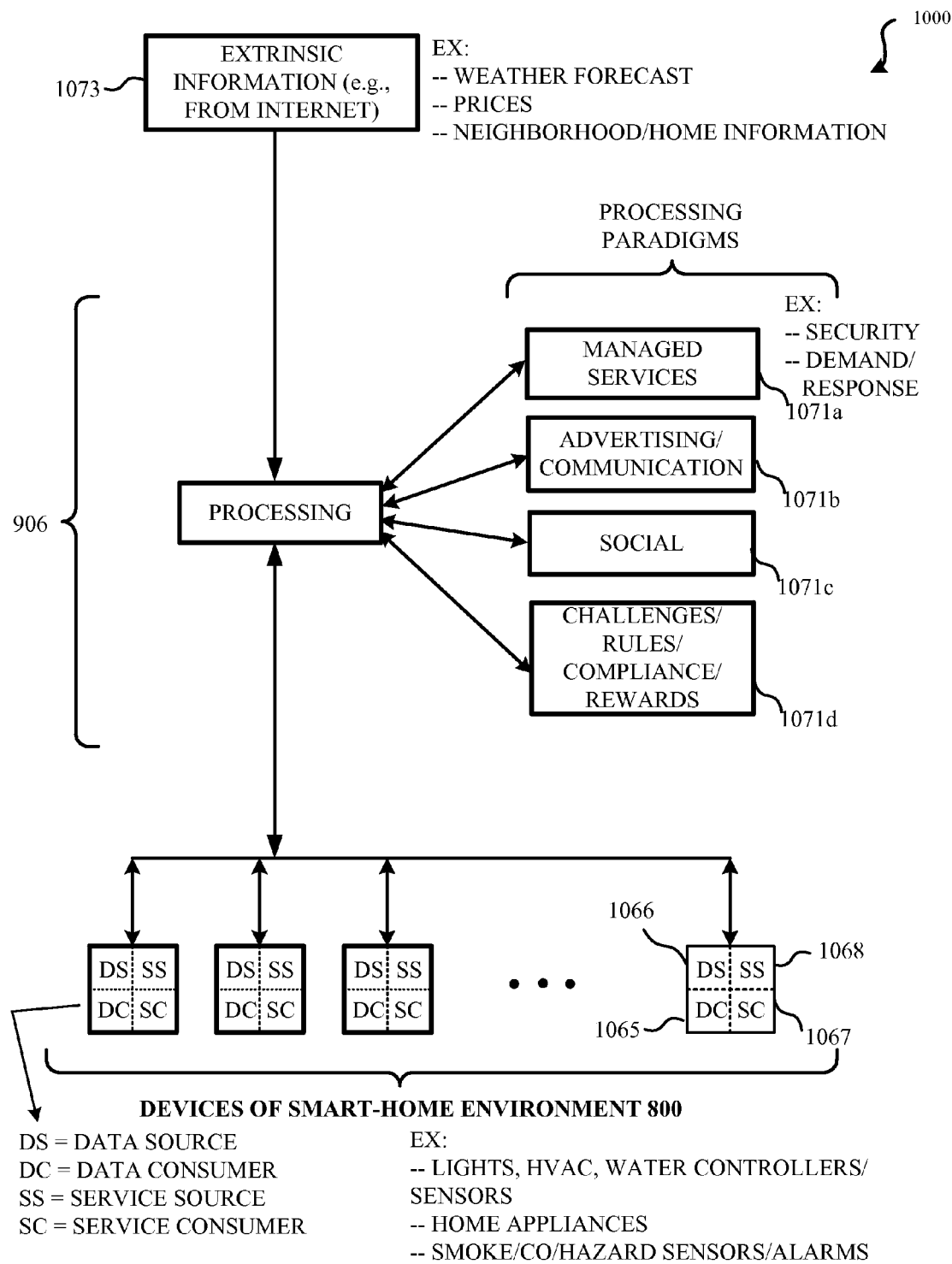
FIG. 10 illustrates an embodiment of an abstracted functional view of the extensible devices and services platform of FIG. 9, with reference to a processing engine as well as devices of the smart-home environment.

FIG. 10 illustrates an abstracted functional view of the extensible devices and services platform 900 of FIG. 9, with particular reference to the processing engine 906 as well as devices, such as those of the smart-home environment 800 of FIG. 8. Even though devices situated in smart-home environments will have an endless variety of different individual capabilities and limitations, they can all be thought of as sharing common characteristics in that each of them is a data consumer 1065 (DC), a data source 1066 (DS), a services consumer 1067 (SC), and a services source 1068 (SS). Advantageously, in addition to providing the essential control information needed for the devices to achieve their local and immediate objectives, the extensible devices and services platform 900 can also be configured to harness the large amount of data that is flowing out of these devices. In addition to enhancing or optimizing the actual operation of the devices themselves with respect to their immediate functions, the extensible devices and services platform 900 can be directed to "repurposing" that data in a variety of automated, extensible, flexible, and/or scalable ways to achieve a variety of useful objectives. These objectives may be predefined or adaptively identified based on, e.g., usage patterns, device efficiency, and/or user input (e.g., requesting specific functionality).

For example, FIG. 10 shows processing engine 906 as including a number of paradigms 1071. Processing engine 906 can include a managed services paradigm 1071*a* that monitors and manages primary or secondary device functions. The device functions can include ensuring proper operation of a device given user inputs, estimating that (e.g., and responding to an instance in which) an intruder is or is attempting to be in a dwelling, detecting a failure of equipment coupled to the device (e.g., a light bulb having burned out), implementing or otherwise responding to energy demand response events, or alerting a user of a current or predicted future event or characteristic. Processing engine 906 can further include an advertising/communication paradigm 1071*b* that estimates characteristics (e.g., demographic information), desires and/or products of interest of a user based on device usage. Services, promotions, products or upgrades can then be offered or automatically provided to the user. Processing engine 906 can further include a social paradigm 1071*c* that uses information from a social network, provides information to a social network (for example, based on device usage), and/or processes data associated with user and/or device interactions with the social network platform. For example, a user's status as reported to his trusted contacts on the social network could be updated to indicate when he is home based on light detection, security system inactivation or device usage detectors. As another example, a user may be able to share device-usage statistics with other users. In yet another example, a user may share HVAC settings that result in low power bills and other users may download the HVAC settings to their smart thermostat 802 to reduce their power bills.

The processing engine 906 can include a challenges/rules/compliance/rewards paradigm 1071*d* that informs a user of challenges, competitions, rules, compliance regulations and/or rewards and/or that uses operation data to determine whether a challenge has been met, a rule or regulation has been complied with and/or a reward has been earned. The challenges, rules or regulations can relate to efforts to conserve energy, to live safely (e.g., reducing exposure to toxins or carcinogens), to conserve money and/or equipment life, to improve health, etc. For example, one challenge may involve participants turning down their thermostat by one degree for one week. Those that successfully complete the challenge are rewarded, such as by coupons, virtual currency, status, etc. Regarding compliance, an example involves a rental-property owner making a rule that no renters are permitted to access certain owner's rooms. The devices in the room having occupancy sensors could send updates to the owner when the room is accessed.

The processing engine 906 can integrate or otherwise utilize extrinsic information 1073 from extrinsic sources to improve the functioning of one or more processing paradigms. Extrinsic information 1073 can be used to interpret data received from a device, to determine a characteristic of the environment near the device (e.g., outside a structure that the device is enclosed in), to determine services or products available to the user, to identify a social network or social-network information, to determine contact information of entities (e.g., public-service entities such as an emergency-response team, the police or a hospital) near the device, etc., to identify statistical or environmental conditions, trends or other information associated with a home or neighborhood, and so forth.

An extraordinary range and variety of benefits can be brought about by, and fit within the scope of, the described extensible devices and services platform 900, ranging from the ordinary to the profound. Thus, in one "ordinary" example, each bedroom of the smart-home environment 800 can be provided with a smart wall switch 808, a smart wall plug 810, and/or smart hazard detectors 804, all or some of which include an occupancy sensor, wherein the occupancy sensor is also capable of inferring (e.g., by virtue of motion detection, facial recognition, audible sound patterns, etc.) whether the occupant is asleep or awake. If a serious fire event is sensed, the remote security/monitoring service or fire department is advised of how many occupants there are in each bedroom, and whether those occupants are still asleep (or immobile) or whether they have properly evacuated the bedroom. While this is, of course, a very advantageous capability accommodated by the described extensible devices and services platform, there can be substantially more "profound" examples that can truly illustrate the potential of a larger "intelligence" that can be made available. By way of perhaps a more "profound" example, the same bedroom occupancy data that is being used for fire safety can also be "repurposed" by the processing engine 906 in the context of a social paradigm of neighborhood child development and education. Thus, for example, the same bedroom occupancy and motion data discussed in the "ordinary" example can be collected and made available (properly anonymized) for processing in which the sleep patterns of schoolchildren in a particular ZIP code can be identified and tracked. Localized variations in the sleeping patterns of the schoolchildren may be identified and correlated, for example, to different nutrition programs in local schools.

Figure 11:
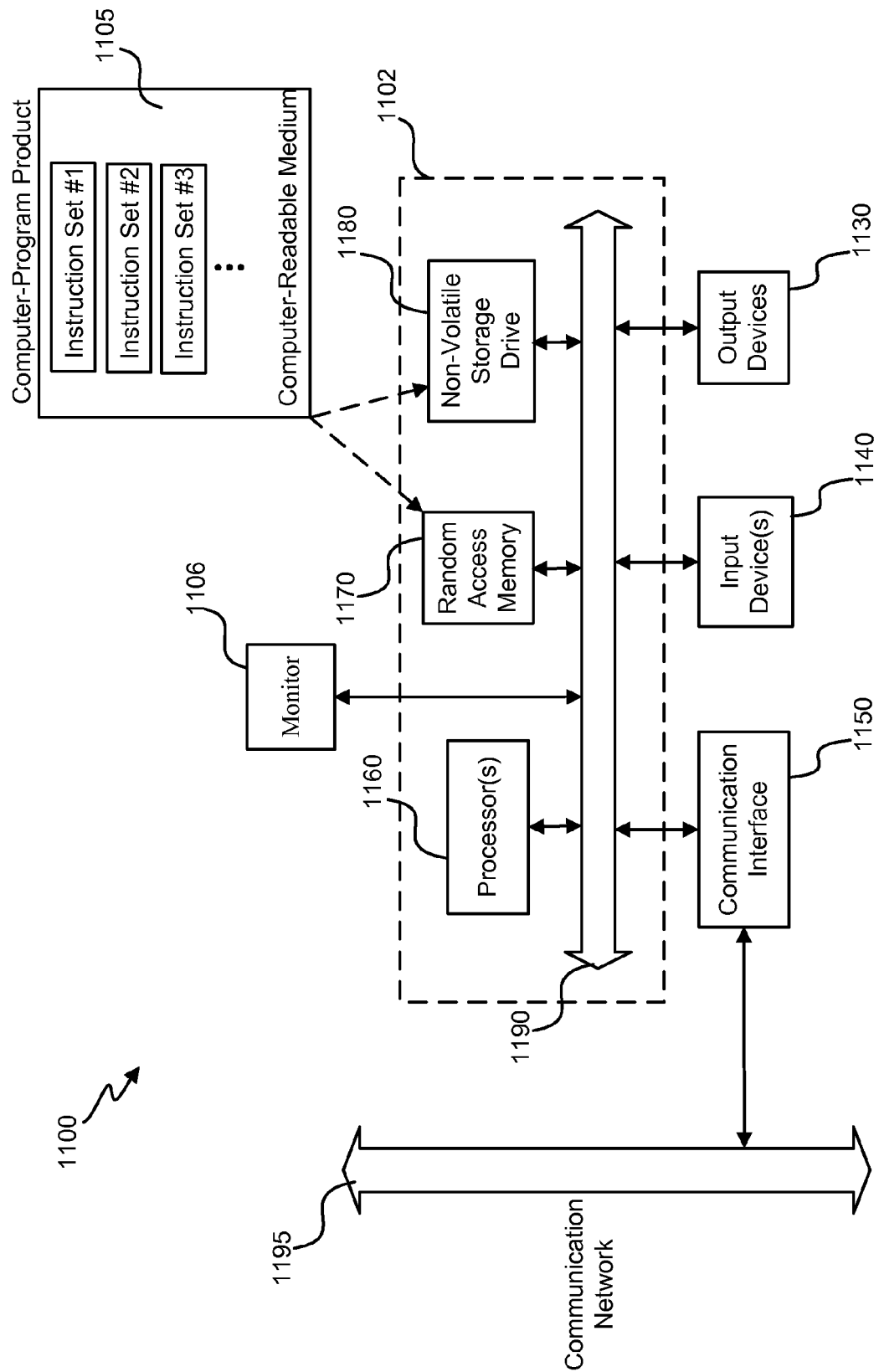
FIG. 11 illustrates an embodiment of a computer system.
Figure 14:
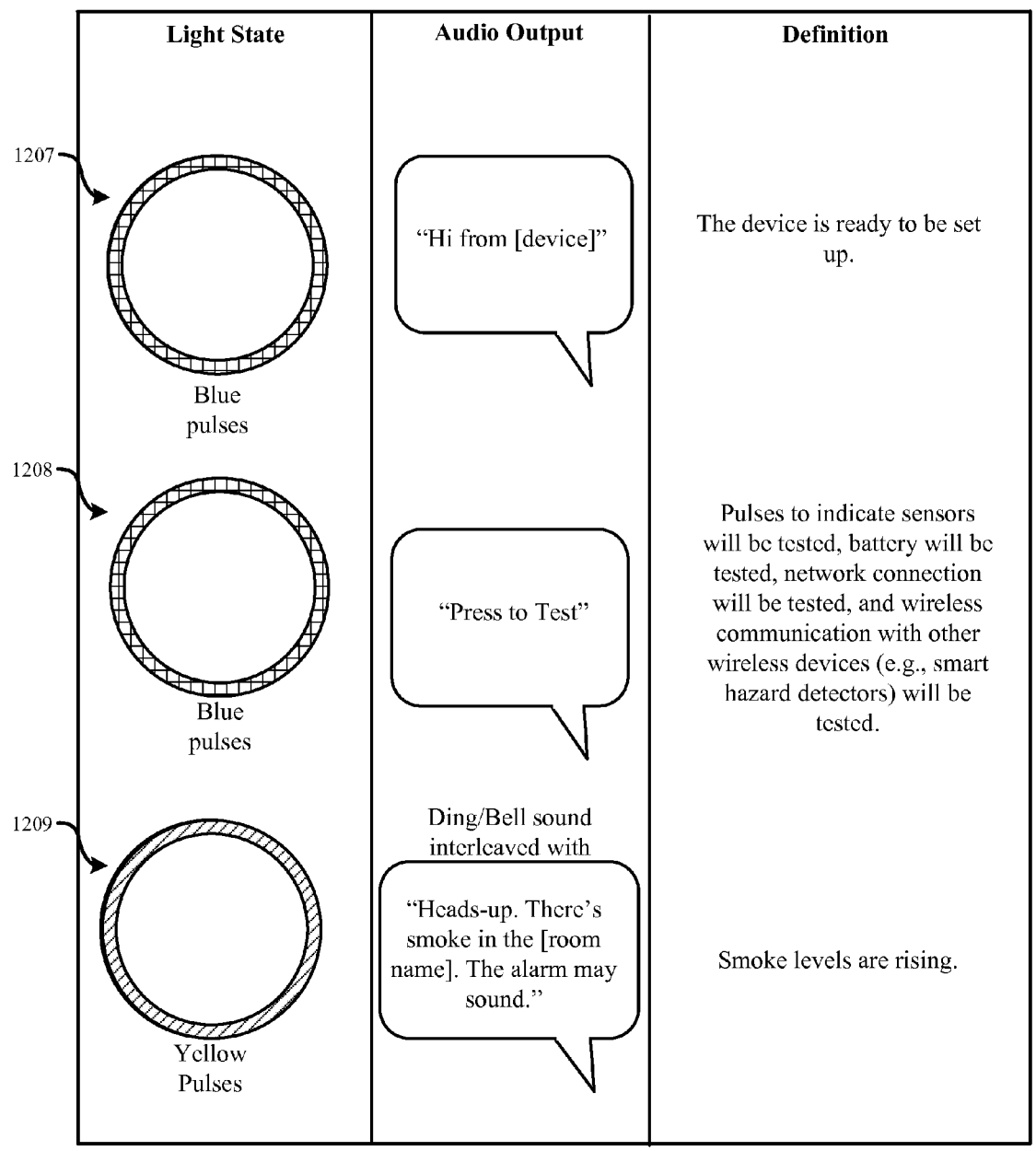
Figure 17:
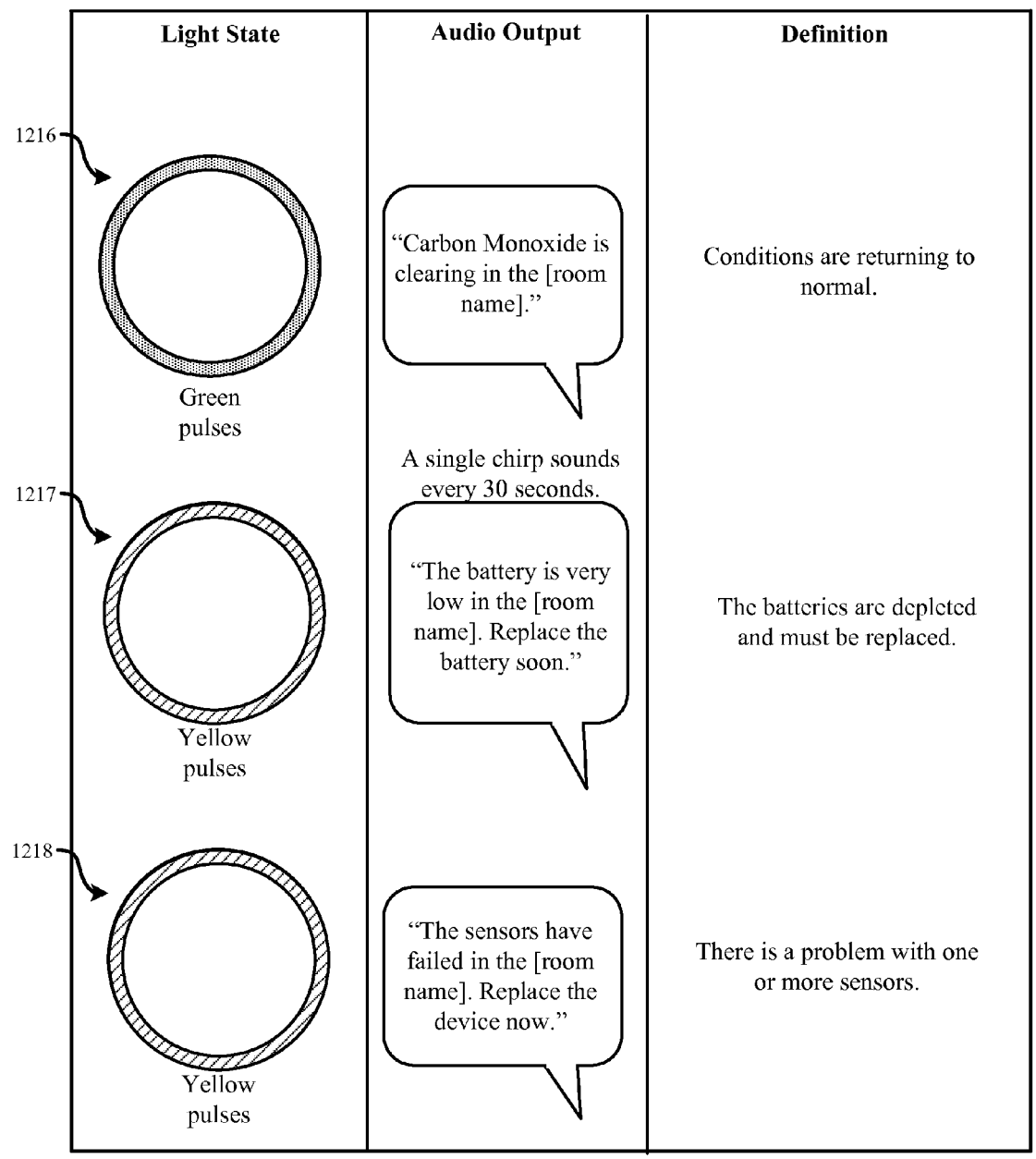

With reference to FIG. 11, an embodiment of a special-purpose computer system 1100 is shown. For example, one or more intelligent components, processing system 110 and components thereof may be a special-purpose computer system 1100. Such a special-purpose computer system 1100 may be incorporated as part of a hazard detector and/or any of the other computerized devices discussed herein, such as a remote server, smart thermostat, or network. The above methods may be implemented by computer-program products that direct a computer system to perform the actions of the above-described methods and components. Each such computer-program product may comprise sets of instructions (codes) embodied on a computer-readable medium that direct the processor of a computer system to perform corresponding actions. The instructions may be configured to run in sequential order, or in parallel (such as under different processing threads), or in a combination thereof. After loading the computer-program products on a general purpose computer system 1126, it is transformed into the special-purpose computer system 1100.

Special-purpose computer system 1100 comprises a computer 1102, a monitor 1106 coupled to computer 1102, one or more additional user output devices 1130 (optional) coupled to computer 1102, one or more user input devices 1140 (e.g., keyboard, mouse, track ball, touch screen) coupled to computer 1102, an optional communications interface 1150 coupled to computer 1102, a computer-program product 1105 stored in a tangible computer-readable memory in computer 1102. Computer-program product 1105 directs computer system 1100 to perform the above-described methods. Computer 1102 may include one or more processors 1160 that communicate with a number of peripheral devices via a bus subsystem 1190. These peripheral devices may include user output device(s) 1130, user input device(s) 1140, communications interface 1150, and a storage subsystem, such as random access memory (RAM) 1170 and non-volatile storage drive 1180 (e.g., disk drive, optical drive, solid state drive), which are forms of tangible computer-readable memory.

Computer-program product 1105 may be stored in non-volatile storage drive 1180 or another computer-readable medium accessible to computer 1102 and loaded into random access memory (RAM) 1170. Each processor 1160 may comprise a microprocessor, such as a microprocessor from Intel® or Advanced Micro Devices, Inc.®, or the like. To support computer-program product 1105, the computer 1102 runs an operating system that handles the communications of computer-program product 1105 with the above-noted components, as well as the communications between the above-noted components in support of the computer-program product 1105. Exemplary operating systems include Windows® or the like from Microsoft Corporation, Solaris® from Sun Microsystems, LINUX, UNIX, and the like.

User input devices 1140 include all possible types of devices and mechanisms to input information to computer 1102. These may include a keyboard, a keypad, a mouse, a scanner, a digital drawing pad, a touch screen incorporated into the display, audio input devices such as voice recognition systems, microphones, and other types of input devices. In various embodiments, user input devices 1140 are typically embodied as a computer mouse, a trackball, a track pad, a joystick, wireless remote, a drawing tablet, a voice command system. User input devices 1140 typically allow a user to select objects, icons, text and the like that appear on the monitor 1106 via a command such as a click of a button or the like. User output devices 1130 include all possible types of devices and mechanisms to output information from computer 1102. These may include a display (e.g., monitor 1106), printers, non-visual displays such as audio output devices, etc.

Communications interface 1150 provides an interface to other communication networks, such as communication network 1195, and devices and may serve as an interface to receive data from and transmit data to other systems, WANs and/or the Internet. Embodiments of communications interface 1150 typically include an Ethernet card, a modem (telephone, satellite, cable, ISDN), a (asynchronous) digital subscriber line (DSL) unit, a FireWire® interface, a USB® interface, a wireless network adapter, and the like. For example, communications interface 1150 may be coupled to a computer network, to a FireWire® bus, or the like. In other embodiments, communications interface 1150 may be physically integrated on the motherboard of computer 1102, and/or may be a software program, or the like.

RAM 1170 and non-volatile storage drive 1180 are examples of tangible computer-readable media configured to store data such as computer-program product embodiments of the present invention, including executable computer code, human-readable code, or the like. Other types of tangible computer-readable media include floppy disks, removable hard disks, optical storage media such as CD-ROMs, DVDs, bar codes, semiconductor memories such as flash memories, read-only-memories (ROMs), battery-backed volatile memories, networked storage devices, and the like. RAM 1170 and non-volatile storage drive 1180 may be configured to store the basic programming and data constructs that provide the functionality of various embodiments of the present invention, as described above.

Software instruction sets that provide the functionality of the present invention may be stored in RAM 1170 and non-volatile storage drive 1180. These instruction sets or code may be executed by the processor(s) 1160. RAM 1170 and non-volatile storage drive 1180 may also provide a repository to store data and data structures used in accordance with the present invention. RAM 1170 and non-volatile storage drive 1180 may include a number of memories including a main random access memory (RAM) to store instructions and data during program execution and a read-only memory (ROM) in which fixed instructions are stored. RAM 1170 and non-volatile storage drive 1180 may include a file storage subsystem providing persistent (non-volatile) storage of program and/or data files. RAM 1170 and non-volatile storage drive 1180 may also include removable storage systems, such as removable flash memory.

Bus subsystem 1190 provides a mechanism to allow the various components and subsystems of computer 1102 to communicate with each other as intended. Although bus subsystem 1190 is shown schematically as a single bus, alternative embodiments of the bus subsystem may utilize multiple busses or communication paths within the computer 1102.

FIGS. 12-18 represent various illumination states that may be output by a hazard detector, such as the hazard detectors and other smart-home devices detailed herein. Such illumination states may involve various colors and animations. Synthesized or recorded spoken audio messages may accompany at least some of such illumination states as detailed in the charts of FIGS. 12-18. The majority of the time, it can be expected that no light of a hazard detector will be illuminated. When the light is illuminated, the hazard detector is conveying a message (other than if light state 1203 is illuminated). States 1201 and 1202, which involve blue and green illumination, are illustrated in FIG. 12 and may be presented during a set up process. State 1203 involves a conditional illumination state, which can be referred to as a "path light" state. Such a state may be illuminated in response to motion and the brightness level in an ambient environment of a hazard detector dropping below a threshold brightness level. States 1204 and 1205 represent pre-alarm (pre-alert or early warning) states and emergency (alert or alarm) states. State 1206 may be for a separate light of the hazard detector that is indicative of if a wired (e.g., non-battery) power source is connected and available, such as a household's 120 V AC power supply. State 1207 may be used as part of a setup process. For instance, "[device]" may be replaced with a spoken indication of the brand name of the hazard detector. State 1208 may be presented when a user presses a button to test the hazard detector. State 1209 may represent a state that is indicative of a potential danger and may server as an early warning. For state 1209 (and other states having a similar designation), [room type] may be replaced with a spoken indication of the type of room in which the hazard detector is installed. At the time of installation, a user may have specified to the hazard detector, such as via a selection menu, the type of room in which the hazard detector was being installed. States 1210 and 1211 represent additional pre-alarm states. States 1212, 1213, and 1214 represent various alarm (alert) states. State 1215 may be output when a smoke hazard is clearing. State 1216 may be output when a carbon monoxide hazard is clearing. States 1217, 1218, 1219, 1220, 1221 represent states output in response to a status check that identifies a problem with the hazard detector. Such a state being output may require one or more user actions to resolve.

Preferably, the voice advisories during emergency-level alerts are interleaved in time during silent periods between loud, shrieking tonal alarm patterns, so as to comply with regulations such as National Fire Protection Association (NFPA) and Underwriters Laboratories (UL) standards that require a maximum silence period between tonal alarm patterns of 1.5 seconds (Ref UL2034, UL217, NFPA72 and NFPA720).

It should be understood that the above detailed illumination states and audio messages are merely exemplary. In various other embodiments, the colors, animations, definitions and/or audio messages may be modified.

In order to provide input to various embodiments of the hazard detectors detailed herein, it may be possible to perform a gesture to provide input, which may result in silencing "nuisance" alarms—that is, alarms triggered by a non-hazardous condition (e.g., burning toast). Within a distance of approximately 2-6 feet of the hazard detector, a wave of a user's hand and arm can be detected. In some embodiments, multiple waves must be performed for the gesture to be detected. As detailed in relation to FIG. 19, some of the pre-alert or alert states may silenced, at least temporarily, by using a wave gesture. In some situations, as noted in FIG. 19, certain situations preclude the alarm from being silenced. A wave gesture can also be used for canceling a manual test and/or to hear a detailed message when a visual status is being presented via illumination. In some embodiments, rather than performing a gesture, a user may push a button (or physically actuate some other part) of the hazard detector.

If multiple hazard detectors are present, all of the hazard detectors may output light and sound of a heads-up (pre-alert) or emergency (alert) situation is present. To silence an alarm (either in the pre-alert or alert state), the user may be required to perform the gesture (or push a button) at the hazard detector that originally detected the hazard. Once the proper hazard detector is silenced, each other hazard detector may be silenced (based on wireless communication between the hazard detectors).

Figure 20:
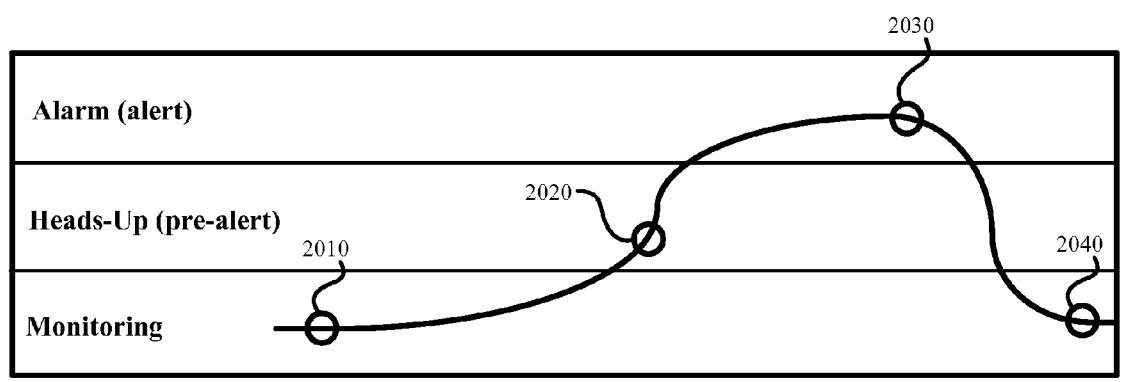
FIG. 20 illustrates an exemplary situation of when a heads-up (pre-alert) state is used prior to an alarm (emergency) state.

Referring to FIG. 20, an exemplary situation of when a heads-up (pre-alert) state is used. A gentle heads-up (pre-alert) warns a user of a condition that has risen above normal, but has not yet triggered a full alert (emergency) state. Sounds and messages output during a pre-alert state are intended to be less irritating and urgent than messages during an alert state. By having such a pre-alarm state, users may be less likely to disable a hazard detector and, thus, the hazard detector may be more likely to be functioning when needed.

As an example, at point 2010, the hazard detector is monitoring its ambient environment for hazards, such as smoke and carbon monoxide. An increased level of carbon monoxide or smoke may be detected at point 2020. At such point, a pre-alert message and illumination may be output to warn users of the impending conditions. Such a pre-alert may involve a notable, but non jarring (in comparison to a shrieking emergency alarm sound), bell or ringing sound. The notable but non-jarring sound may be similar in intensity to the bell sound emitted by an elevator when arriving at the target floor, which is enough to notify but not so much as to unpleasantly jar the user. A user may be permitted to silence such a heads-up (pre-alert) message. At point 2030, a full alarm may be sounded, which may involve a loud, shrill alarm sound. At point 2040, a message (with an accompanying illumination state) may be output indicative of normal conditions resuming. Heads-up (pre-alert) states are associated with a yellow illumination state while emergency (alert) states are associated with red illumination states. If the hazard level in the environment of the hazard detector rises quickly, no pre-alert state may be entered by the hazard detector. Rather, the alarm state may be directly entered from a monitoring state.

It should be noted that the methods, systems, and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known, processes, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

What is claimed is:

1. A method for detecting that a hazardous condition is easing, the method comprising:
   measuring, by a hazard detector, a first amount of the hazardous condition present in an ambient environment of the hazard detector;
   setting, by the hazard detector, a mode of the hazard detector to a pre-alarm state based on the measured first amount of the hazardous condition;

measuring, by the hazard detector, a second amount of the hazardous condition present in the ambient environment of the hazard detector, wherein the second amount is less than the first amount;

determining, by the hazard detector, based on the second amount of the hazardous condition present in the ambient environment, to set the mode to a non-alarm state; and in response to determining, at least partially based on the second amount of the hazardous condition present in the ambient environment to set the mode of the hazard detector to the non-alarm state from the pre-alarm state or an alarm state, outputting an indication that the hazardous condition has eased, wherein:

the hazardous condition having eased indicates the hazardous condition in the ambient environment of the hazard detector has decreased in amount.

2. The method for detecting that the hazardous condition is easing of claim 1, wherein the indication output comprises an auditory message that comprises speech being output by a speaker of the hazard detector.

3. The method for detecting that the hazardous condition is easing of claim 2, further comprising:

accessing, by the hazard detector, a stored indication of a location at which the hazard detector is installed, wherein the auditory message comprises speech indicative of the location.

4. The method for detecting that the hazardous condition is easing of claim 1, wherein the indication output comprises a light of the hazard detector outputting a color indicative of the non-alarm state.

5. The method for detecting that the hazardous condition is easing of claim 1, further comprising:

in response to determining, at least partially based on the first amount of the hazardous condition present in the ambient environment to set the mode of the hazard detector to the pre-alarm state, outputting an indication of the pre-alarm state comprising an auditory message.

6. The method for detecting that the hazardous condition is easing of claim 5, wherein outputting the indication of the pre-alarm state comprising outputting pulsing light of a color indicative of the pre-alarm state.

7. The method for detecting that the hazardous condition is easing of claim 1, further comprising:

measuring, by the hazard detector, a third amount of the hazardous condition present in the ambient environment of the hazard detector, wherein the third amount is greater than the first amount and the second amount; and determining, by the hazard detector, at least partially based on the third amount of the hazardous condition present in the ambient environment, to set the mode to an alarm state, wherein the alarm state causes an alarm of the hazard detector to be sounded.

8. The method for detecting that the hazardous condition is easing of claim 1, further comprising:

determining, by the hazard detector, that a threshold period of time has elapsed while an amount of hazardous condition present in the ambient environment of the hazard detector has remained below a stored hazardous condition value, wherein determining to set the mode to a non-alarm state is further based on determining the threshold period of time has elapsed while the amount of hazardous condition present in the ambient environment of the hazard detector has remained below the stored hazardous condition value.

9. A hazard detector comprising:

a hazard sensor that measures amounts of a hazardous condition present in an ambient environment of the hazard detector;

an output component that outputs information; and a processing system that comprises one or more processors, the processing system being in communication with the output component and the hazard sensor, the processing system being configured to:

receive a first measurement of a first amount of the hazardous condition present in an ambient environment of the hazard detector from the hazard sensor;

set a mode of the hazard detector to a pre-alarm or alarm state based on the first measurement;

receive a second measurement of a second amount of the hazardous condition present in the ambient environment of the hazard detector from the hazard sensor;

determine, based on the second measurement, to set the mode to a non-alarm state in response to determining, at least partially based on the second amount of the hazardous condition present in the ambient environment to set the mode of the hazard detector to the non-alarm state from the alarm state or the pre-alarm state, cause an indication that the hazardous condition has eased to be output by the output component, wherein the hazardous condition having eased indicates the hazardous condition in the ambient environment of the hazard detector has dissipated.

10. The hazard detector of claim 9, wherein the indication output by the output component comprises an auditory message that comprises speech.

11. The hazard detector of claim 10, wherein the processing system is further configured to access a stored indication of a location at which the hazard detector is installed, wherein the auditory message comprises speech indicative of the location.

12. The hazard detector of claim 9, wherein the indication output comprises a light of the output component outputting colored light indicative of the non-alarm state.

13. The hazard detector of claim 9, wherein the processing system is further configured to:

in response to determining to set the mode of the hazard detector to the pre-alarm state, cause an indication of the pre-alarm state to be output by the output component, the indication comprising an auditory message.

14. The hazard detector of claim 13, wherein the output device outputting the indication of the pre-alarm state comprises the output device outputting pulsing light of a color indicative of the pre-alarm state.

15. The hazard detector of claim 9, wherein the processing system is further configured to:

receive a third measurement of a third amount of the hazardous condition present in the ambient environment of the hazard detector from the hazard sensor, wherein the third amount is greater than the first amount and the second amount; and determine, at least partially based on the third measurement, to set the mode to an alarm state, wherein the alarm state causes an alarm of the hazard detector to be sounded.

16. The hazard detector of claim 9, wherein the processing system is further configured to:

determine that a threshold period of time has elapsed while an amount of the hazardous condition, as measured by the hazard sensor, present in the ambient environment has remained below a stored hazardous condition value, wherein the one or more processors being configured to determine to set the mode to a non-alarm state is further based on determining the threshold period of time has elapsed while the amount of the hazardous condition present in the ambient environment has remained below the stored hazardous condition value.

17. A non-transitory processor-readable medium for a hazard detector, comprising processor-readable instructions configured to cause one or more processors of the hazard detector to:

receive a first measurement of a first amount of the hazardous condition present in an ambient environment of the hazard detector from the hazard sensor;

set a mode of the hazard detector to a pre-alarm or alarm state based on the first measurement;

receive a second measurement of a second amount of the hazardous condition present in the ambient environment of the hazard detector from the hazard sensor;

determine, based on the second measurement, to set the mode to a non-alarm state; and in response to determining at least partially based on the second measurement to set the mode of the hazard detector to the non-alarm state, cause an indication that the hazardous condition has eased to be output by the hazard detector, wherein the hazardous condition having eased indicates the hazardous condition in the ambient environment of the hazard detector has decreased in amount.

18. The non-transitory processor-readable medium for the hazard detector of claim 17, further comprising:

accessing a stored indication of a room in which the hazard detector is located, wherein causing the indication that the hazardous condition has eased comprises outputting an auditory message indicative of the room.

\* \* \* \* \*